(12) United States Patent
Blake et al.

(10) Patent No.: US 10,925,511 B2
(45) Date of Patent: Feb. 23, 2021

(54) SYSTEM AND METHOD FOR CARDIAC ABLATION

(71) Applicant: CardioSolv Ablation Technologies, Inc., Boston, MA (US)

(72) Inventors: Robert Blake, Baltimore, MD (US); Scott Kokones, Brookline, MA (US); Brock Tice, Granville, MI (US)

(73) Assignee: CardioSolv Ablation Technologies, Inc., Boston, MA (US)

( * ) Notice: Subject to any disclaimer, the term of this patent is extended or adjusted under 35 U.S.C. 154(b) by 1412 days.

(21) Appl. No.: 14/808,353

(22) Filed: Jul. 24, 2015

(65) Prior Publication Data

US 2016/0022375 A1 Jan. 28, 2016

Related U.S. Application Data

(60) Provisional application No. 62/028,787, filed on Jul. 24, 2014.

(51) Int. Cl.
*A61B 5/00* (2006.01)
*A61B 5/06* (2006.01)
(Continued)

(52) U.S. Cl.
CPC .................. *A61B 5/06* (2013.01); *A61B 5/02* (2013.01); *A61B 5/6844* (2013.01); *A61B 5/742* (2013.01); *A61B 5/746* (2013.01); *A61B 5/7455* (2013.01); *A61B 18/1492* (2013.01); *A61B 34/10* (2016.02); *G06T 7/0012* (2013.01); *G06T 7/11* (2017.01); *G06T 19/00* (2013.01); *G16H 50/00* (2018.01); *A61B 2018/00351* (2013.01); *A61B 2018/00577* (2013.01); *A61B 2018/00642* (2013.01); *A61B 2034/104* (2016.02); *A61B 2034/105* (2016.02);
(Continued)

(58) Field of Classification Search
CPC ...................................... A61B 5/053
See application file for complete search history.

(56) References Cited

U.S. PATENT DOCUMENTS

| | | | |
|---|---|---|---|
| 5,954,665 | A | 9/1999 | Ben-Haim et al. |
| 6,537,272 | B2 | 3/2003 | Christopherson et al. |

(Continued)

OTHER PUBLICATIONS

Invitation to Pay Additional Fees and Communication Relating to the Results of the Partial International Search issued in International Patent Application No. PCT/US2015/041999, dated Sep. 30, 2015.
(Continued)

*Primary Examiner* — Joseph M Santos Rodriguez
(74) *Attorney, Agent, or Firm* — Finnegan, Henderson, Farabow, Garrett & Dunner LLP

(57) ABSTRACT

A system for determining cardiac targets is provided. The system may include at least one processing device configured to carry out instructions to receive cardiac imaging data, segment the cardiac imaging data to identify at least two types of cardiac tissue, generate a cardiac model based on the identified tissue, simulate cardiac activity based on the generated cardiac model, and identify at least one cardiac target based on the simulation. A cardiac therapy system may be utilized to provide feedback to a user in order to guide a cardiac treatment device to a cardiac target.

13 Claims, 14 Drawing Sheets

(51) Int. Cl.

| | | |
|---|---|---|
| *G06T 19/00* | (2011.01) | |
| *G16H 50/00* | (2018.01) | |
| *G06T 7/00* | (2017.01) | |
| *A61B 18/14* | (2006.01) | |
| *A61B 34/10* | (2016.01) | |
| *G06T 7/11* | (2017.01) | |
| *A61B 5/02* | (2006.01) | |
| *A61B 18/00* | (2006.01) | |
| *A61B 90/50* | (2016.01) | |
| *A61B 90/00* | (2016.01) | |
| *A61B 34/20* | (2016.01) | |

(52) U.S. Cl.
CPC . *A61B 2034/2051* (2016.02); *A61B 2090/363* (2016.02); *A61B 2090/502* (2016.02); *A61B 2576/023* (2013.01); *G06T 2207/20128* (2013.01); *G06T 2207/30048* (2013.01)

(56) References Cited

U.S. PATENT DOCUMENTS

| | | | |
|---|---|---|---|
| 6,658,279 B2 | 12/2003 | Swanson et al. | |
| 6,711,429 B1 | 3/2004 | Gilboa et al. | |
| 7,166,075 B2 | 1/2007 | Varghese et al. | |
| 7,306,593 B2 | 12/2007 | Keidar et al. | |
| 7,479,141 B2 | 1/2009 | Kleen et al. | |
| 7,502,642 B2 | 3/2009 | Boese et al. | |
| 7,517,346 B2 | 4/2009 | Sloan et al. | |
| 7,527,625 B2 | 5/2009 | Knight et al. | |
| 7,565,190 B2 | 7/2009 | Okerlund et al. | |
| 7,599,730 B2 | 10/2009 | Hunter et al. | |
| 7,715,907 B2 | 5/2010 | Koertge et al. | |
| 7,892,232 B2 | 2/2011 | Boese et al. | |
| 8,050,739 B2 | 11/2011 | Eck et al. | |
| 8,057,397 B2 | 11/2011 | Li et al. | |
| 8,099,151 B2 | 1/2012 | Halperin et al. | |
| 8,146,603 B2 | 4/2012 | Thapliyal et al. | |
| 8,195,271 B2 | 6/2012 | Rahn | |
| 8,267,927 B2 | 9/2012 | Dalal et al. | |
| 8,295,913 B2 | 10/2012 | Haras | |
| 8,320,711 B2 | 11/2012 | Altman et al. | |
| 8,335,557 B2 | 12/2012 | Maschke | |
| 8,364,242 B2 | 1/2013 | Li | |
| 8,412,307 B2 | 4/2013 | Willis et al. | |
| 8,428,690 B2 | 4/2013 | Li et al. | |
| 8,583,220 B2 | 11/2013 | Schwartz | |
| 8,615,287 B2 | 12/2013 | Harlev et al. | |
| 8,634,896 B2 | 1/2014 | Sra et al. | |
| 8,702,688 B2 | 4/2014 | Melsky | |
| 8,706,195 B2 | 4/2014 | Strommer et al. | |
| 8,755,864 B2 | 6/2014 | Hauck et al. | |
| 8,790,262 B2 | 7/2014 | Li et al. | |
| 8,805,481 B2 | 8/2014 | Sumanaweera et al. | |
| 8,876,817 B2 | 11/2014 | Avitall et al. | |
| 8,886,288 B2 | 11/2014 | Jenkins et al. | |
| 8,900,225 B2 | 12/2014 | Bar-Tal et al. | |
| 8,926,604 B2 | 1/2015 | Govari et al. | |
| 8,954,161 B2 | 2/2015 | McCarthy et al. | |
| 8,979,871 B2 | 3/2015 | Tyc et al. | |
| 9,014,789 B2 | 4/2015 | Mercader et al. | |
| 9,033,893 B2 | 5/2015 | Spector | |
| 9,101,333 B2 | 8/2015 | Schwartz | |
| 9,113,910 B2 | 8/2015 | Pachon Mateos et al. | |
| 9,119,633 B2 | 9/2015 | Gelbart et al. | |
| 9,125,689 B2 | 9/2015 | Mielekamp | |
| 9,144,461 B2 | 9/2015 | Kruecker et al. | |
| 9,173,638 B2 | 11/2015 | Govari et al. | |
| 9,186,081 B2 | 11/2015 | Afonso et al. | |
| 9,192,789 B2 | 11/2015 | Thapliyal et al. | |
| 9,204,927 B2 | 12/2015 | Afonso et al. | |
| 2005/0054918 A1 | 3/2005 | Sra et al. | |
| 2007/0014452 A1 | 1/2007 | Suresh et al. | |
| 2010/0160768 A1 | 6/2010 | Marrouche et al. | |
| 2011/0087110 A1* | 4/2011 | Nathan | A61B 5/053 600/476 |
| 2012/0027278 A1 | 2/2012 | Chaney et al. | |
| 2013/0197881 A1* | 8/2013 | Mansi | A61N 1/3627 703/2 |
| 2014/0058246 A1 | 2/2014 | Boveja et al. | |
| 2014/0058387 A1 | 2/2014 | Kreucker et al. | |
| 2014/0088943 A1 | 3/2014 | Trayanova et al. | |
| 2014/0122048 A1* | 5/2014 | Vadakkumpadan | G06T 7/11 703/11 |
| 2014/0163360 A1 | 6/2014 | Stevens-Wright et al. | |
| 2014/0228835 A1 | 8/2014 | Mielekamp et al. | |
| 2014/0296842 A1 | 10/2014 | Mansi et al. | |
| 2015/0073246 A1 | 3/2015 | Chmiel et al. | |
| 2015/0150643 A1 | 6/2015 | Trayanova et al. | |
| 2015/0305821 A1 | 10/2015 | Lacoste et al. | |

OTHER PUBLICATIONS

International Search Report and Written Opinion issued in International Patent Application No. PCT/US2015/041999, dated Dec. 14, 2015.

* cited by examiner

900

901

900

901

SYSTEM AND METHOD FOR CARDIAC ABLATION

CROSS REFERENCES TO RELATED APPLICATION

This application claims the benefit of priority of U.S. Provisional Patent Application No. 62/028,787, filed on Jul. 24, 2014, which is incorporated herein by reference in its entirety.

TECHNICAL FIELD

The present invention relates to systems and methods for ablating cardiac tissue.

BACKGROUND

Ventricular tachycardia (VT)—a life-threatening heart rhythm characterized by an extremely fast (>100 bpm) heartbeat—frequently occurs in patients with scarring from a previous myocardial infarction (heart attack). In patients suffering from VT, the electrical signal that synchronizes mechanical contraction may be blocked, delayed, or rerouted by non-conductive scar tissue. Depending on the scar geometry, electrical signals in subsequent beats may interact to initiate a never-ending pattern of circuitous electrical propagation called monomorphic VT. VT may eventually devolve into a chaotic cardiac rhythm, i.e., ventricular fibrillation (VF). Under VF conditions, the heart may be unable to pump blood, which can lead to death within minutes. Catheter ablation may be used to burn heart tissue in strategic places to modify the scar geometry and potentially prevent VT from developing. An electrophysiologist (EP), a specialized cardiologist, may use a catheter inserted into the heart to first map electrical propagation and then to selectively burn tissue in order to prevent VT.

When successful, catheter ablation provides an effective cure for VT. However, the catheter ablation procedures have a success rate of approximately 58% at eliminating VT on a first attempt. The low efficacy of the procedure may stem from the low resolution of current mapping techniques and the inability to see the complex three-dimensional (3D) pathways of electrical propagation that are responsible for the initiation and maintenance of VT. Thus, an EP may not only be unable to determine optimal lesion location to prevent or end VT, but he or she may also be unable to ensure that a lesion is placed in a desired location. These limitations result in inaccurate ablation lesion placement and the creation of excessive ablation lesions, prolonging the procedure (currently 4-12 hours) and increasing the risk of major complications such as chamber perforation, thromboemboli, and bleeding. New approaches that provide accurate identification of optimal VT ablation targets and guiding systems that facilitate the placement of lesions at optimal target sites may improve the efficacy of the therapy while reducing post-procedure complications.

The foregoing background description is exemplary only; embodiments of the invention described hereafter are not limited to treating only the above-described conditions.

SUMMARY

Some embodiments of the present disclosure include a system for determining cardiac targets. The system may include a non-transitory computer readable medium comprising instructions and at least one processing device configured to carry out the instructions. The processing device may receive cardiac imaging data, segment the cardiac imaging data to identify at least two types of tissue, generate a cardiac model based on the identified tissue, simulate cardiac activity based on the generated cardiac model, and locate at least one cardiac target based on the simulation.

Some embodiments of the present disclosure may include a cardiac therapy system. The cardiac therapy system may include at least one processing device configured to, cause a mapping system to detect an intracardiac location of an ablation tip of a cardiac ablation catheter, output a cardiac imaging model identifying at least one ablation target to a display, output the intracardiac location of the ablation tip to the display, and cause feedback to be provided to a user, the feedback indicating a proximity of the ablation tip to the at least one ablation target.

DETAILED DESCRIPTION

Figure 1:
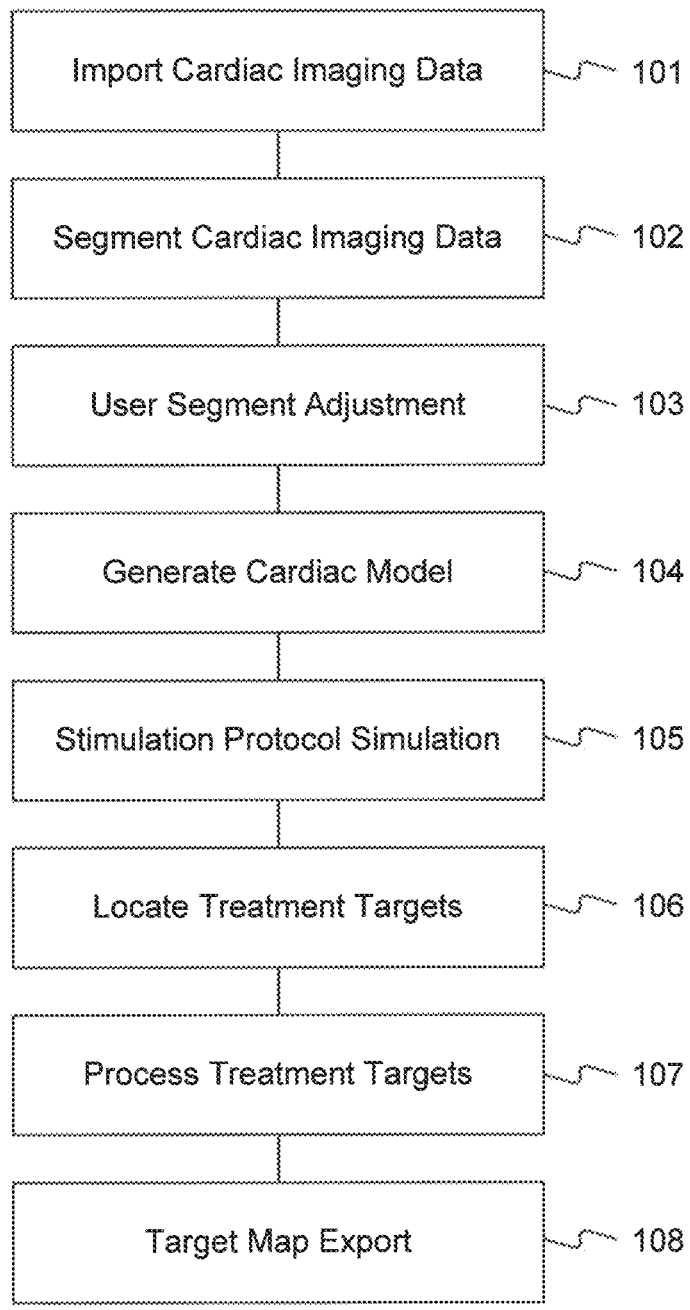
FIG. 1 is a flowchart depicting an exemplary method of determining cardiac targets.

Reference will now be made in detail to exemplary embodiments of the present disclosure, examples of which are illustrated in the accompanying drawings. Wherever possible, the same reference numbers will be used throughout the drawings to refer to the same or like parts. These embodiments are described in sufficient detail to enable those skilled in the art to practice the invention and it is to be understood that other embodiments may be utilized and that changes may be made without departing from the scope of the present invention. The following detailed description, therefore, is not to be interpreted in a limiting sense.

Some embodiments of the present disclosure relate generally to a system and method for guiding and performing a cardiac treatment procedure. Although embodiments of this disclosure are described herein with respect to determining, locating, and identifying treatment targets to address VT in a patient, the disclosure is not limited to these embodiments. Mapping and simulation techniques described herein may further be used to identify treatment targets to address other cardiac conditions, such as atrial fibrillation (AF) or to assess a patient's risk of developing arrhythmias of the ventricle or atria based on their specific anatomy and tissue composition.

As described herein, cardiac imaging data may be analyzed to construct a cardiac model. The cardiac model may include partial differential equations that approximate the electrical activity of the heart. The cardiac model may permit the simulation of propagating electrical activity within the heart. The cardiac model may be analyzed with any suitable analysis technique, such as finite element, finite volume, and finite difference, to simulate electrical activity under various simulated stimulation protocols. In particular, the cardiac model may be used to simulate the induction of VT. Simulations of induced VT may then be analyzed to locate cardiac targets for treatment to potentially reduce or eliminate occurrences of VT, as well as cardiac targets for further study or for stimulation.

Unless otherwise defined, all technical and/or scientific terms used herein have the same meaning as commonly understood by one of ordinary skill in the art to which the embodiments of the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

Embodiments of the methods and techniques disclosed herein may be implemented as instructions to be carried out by at least one processing device. As used herein, the term "processing device" may include an electric circuit that performs a logic operation on an input or inputs. For example, such a processing device may include one or more integrated circuits, microchips, microcontrollers, microprocessors, all or part of a central processing unit (CPU), graphics processing unit (GPU), digital signal processors (DSP), field-programmable gate array (FPGA) or other circuit suitable for executing instructions or performing logic operations. The at least one processing device may be configured to perform an action if it is provided with access to, is programmed with, includes, or is otherwise made capable of carrying out instructions for performing the action. The at least one processing device may be provided with such instructions either directly through information permanently or temporarily maintained in the processing device, or through instructions accessed by or provided to the processing device. Instructions provided to the processing device may be provided in the form of a computer program comprising instructions tangibly embodied on an information carrier, e.g., in a machine-readable storage device, or any tangible, non-transitory, computer-readable medium. A non-transitory, computer-readable medium may include, but is not limited to, a hard drive, an optical disc, flash memory, random access memory, read only memory, processor cache memory, and any other suitable form of data storage. A computer program may be written in any form of programming language, including compiled or interpreted languages, and it can be deployed in any form, including as a standalone program or as one or more modules, components, subroutines, or other unit suitable for use in a computing environment. The at least one processing device may include specialized hardware, general hardware, or a combination of both to execute related instructions. The processing device may also include an integrated communications interface, or a communications interface may be included separate and apart from the processing device. The at least one processing device may be configured to perform a specified function through a connection to a memory location or storage device in which instructions to perform that function are stored. The at least one processing device may also include more than one processing device configured to operate in concert, either serially or in parallel, to carry out the methods and techniques described herein.

Exemplary disclosed embodiments may include devices and methods for determining or identifying cardiac targets. Cardiac targets may include, for example, treatment targets, study targets, and stimulation targets.

Cardiac treatment targets may include cardiac tissue locations designated for treatment. In some embodiments as disclosed herein, a cardiac treatment target may be a cardiac tissue location designated for treatment via a radiofrequency (RF) ablation catheter. Other forms of treatment may include cryoablation, laser ablation, ultrasonic ablation, microwave ablation, gene therapy, and others. Targets may be selected or determined in order to provide treatment for a cardiac condition. For example, in patient's that suffer from VT, targets may be selected such that, when ablated, the patient's VT condition is diminished or eliminated. In some embodiments, targets may be selected to eliminate the electrophysiologic triggers that initiate VT. In some embodiments, targets may be selected to facilitate the treatment of AF and other cardiac conditions.

Cardiac study targets may include cardiac tissue locations designated for further study. For example, some embodiments of the present disclosure include cardiac imaging and/or mapping steps. Identified cardiac study targets may be targets designated for more in-depth or higher resolution imaging and/or mapping. In some circumstances, a physician may not wish to rely solely on model simulations to determine cardiac treatment targets. Thus, a physician may use the disclosed system to suggest cardiac study targets for mapping and then use both model simulation data and mapping data to determine a treatment plan.

In some embodiments consistent with the present disclosure, cardiac targets may be identified as stimulation targets. For example, a physician may wish to determine which of several identified potential VT pathways is most likely to present clinically. A physician may use the system to identify cardiac stimulation locations that, when stimulated, entrain a tachycardic rhythm in the heart. Thus, a physician may use the system as a guide to determine whether an identified potential VT pathway is likely to activate and cause VT in a patient.

For exemplary purposes only, methods discussed herein are discussed with reference to treatment targets. The methods discussed herein for determining, selecting, and identifying targets may, however, be used for the identification of any one of treatment targets, study targets, and stimulation targets.

FIG. 1 is a flowchart depicting an exemplary method of determining cardiac targets. The method as shown in FIG. 1 may be implemented by at least one processing device configured to carry out instructions.

Cardiac target determination method 100 may import cardiac imaging data at import step 101. In import step 101, a patient with ventricular tachycardia may be imaged using standard imaging techniques such as magnetic resonance imaging (MRI), computed tomography (CT), echocardiogram, positron emission tomography, CINE imaging techniques such as cinefluoroscopy and multi-echo, and others. In one embodiment, a gadolinium enhanced MRI is taken of the person's heart. Prior to an MRI, a patient may be injected with a gadolinium containing contrast agent. The additional contrast created by the gadolinium agent circulating in the cardiac tissue permits the differential identification of healthy and scar cardiac tissue.

At import step 101, cardiac imaging data may be imported or received into a processing machine including at least one processing device configured to receive the cardiac imaging data. The at least one processing device may be part of, for example, a personal computer, a computer cluster, and a cardiac mapping and ablation system. Cardiac imaging data may be transferred from the imaging machine via a variety of methods including but not limited to CD, DVD, USB flash disk, FTP, external hard drive, local or remote PACS, or any other method for transferring DICOM or other medical images. The processing machine may further be configured with a terminal for viewing and manipulating the imaging information. In some embodiments, the processing machine may be accessed via a website or a web-portal.

At segmentation step 102, the cardiac imaging data may be segmented to identify at least two types of cardiac tissue. Once the data has been imported onto the processing machine, the imaging data may be processed using a variety of different methods to segment out regions of interest and identify types of cardiac tissue within the patient's cardiac geometry. Identified types of cardiac tissue may include, for example, healthy tissue, electrically non-viable dense scar tissue, and partially electrically viable border zone tissue. Border tissue may include damaged or otherwise unhealthy tissue that retains some electrical properties and may be able to assist in the propagation of an activation signal through the tissue. Border tissue may behave less predictably than healthy tissue. Border tissue may include tissue of a peri-infarct zone, and gray tissue. These types of tissue may be identified within the patient's atria and ventricles.

Cardiac geometry may be segmented using manual, automated, and user-guided semi-automated processes. Semi- or fully-automated methods of segmentation may include image processing techniques such as full width at half maximum, combinations of gray-level thresholding and level-set segmentation, Gaussian diffusion filters, cropping, atlas-based approaches such as large deformation diffeomorphic metric mapping (LDDMM), statistical analysis of intensity levels, and any other suitable image processing technique known in the art. Segmentation may be assisted by any suitable imaging techniques, for example, magnetic resonance imaging (MRI), computed tomography (CT), echocardiogram, positron emission tomography, CINE imaging techniques such as cinefluoroscopy and multi-echo, and any other suitable techniques.

When segmentation has been completed, identified cardiac tissue segments may be displayed to a user. In one embodiment, each tissue type is shown with a different color. Scar tissue is assigned a first color, healthy tissue is assigned a second color and (if shown) border zone may be assigned a third color. Distinct and definitive lines may be shown between each color. In another embodiment, multiple levels of scar tissue beyond two may be identified, and the borders between tissue types may be displayed as gradients between the different colors obscuring the definitive line between these zones. Gradients may be based, for example, on levels of scar tissue identified. In another embodiment, each identified cardiac tissue type may be shown as a different shade or hue of the same color. For example, scar tissue may be shown as dark blue, border zone tissue as medium blue and healthy tissue as light blue.

Figure 2A:
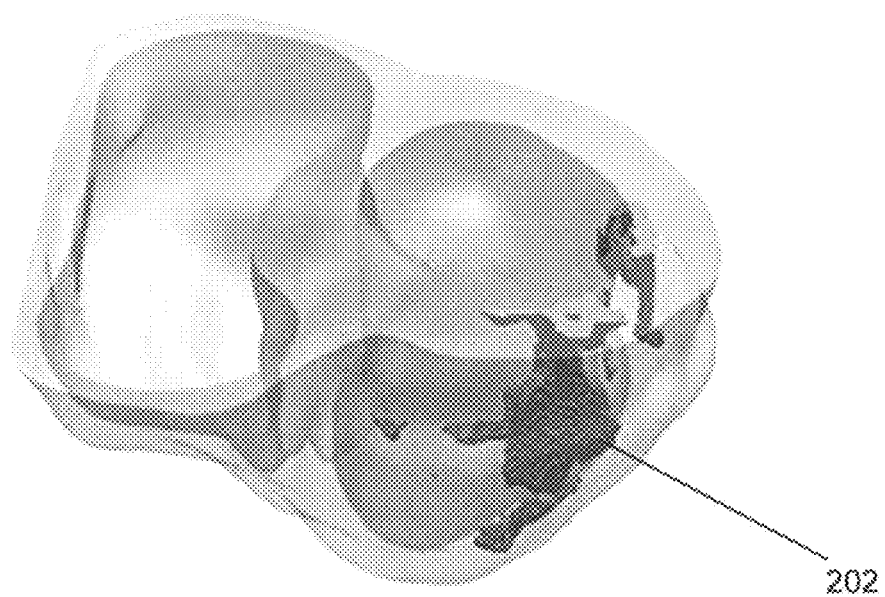
FIGS. 2a and 2b provide exemplary images of a heart with identified cardiac tissue.
Figure 2B:
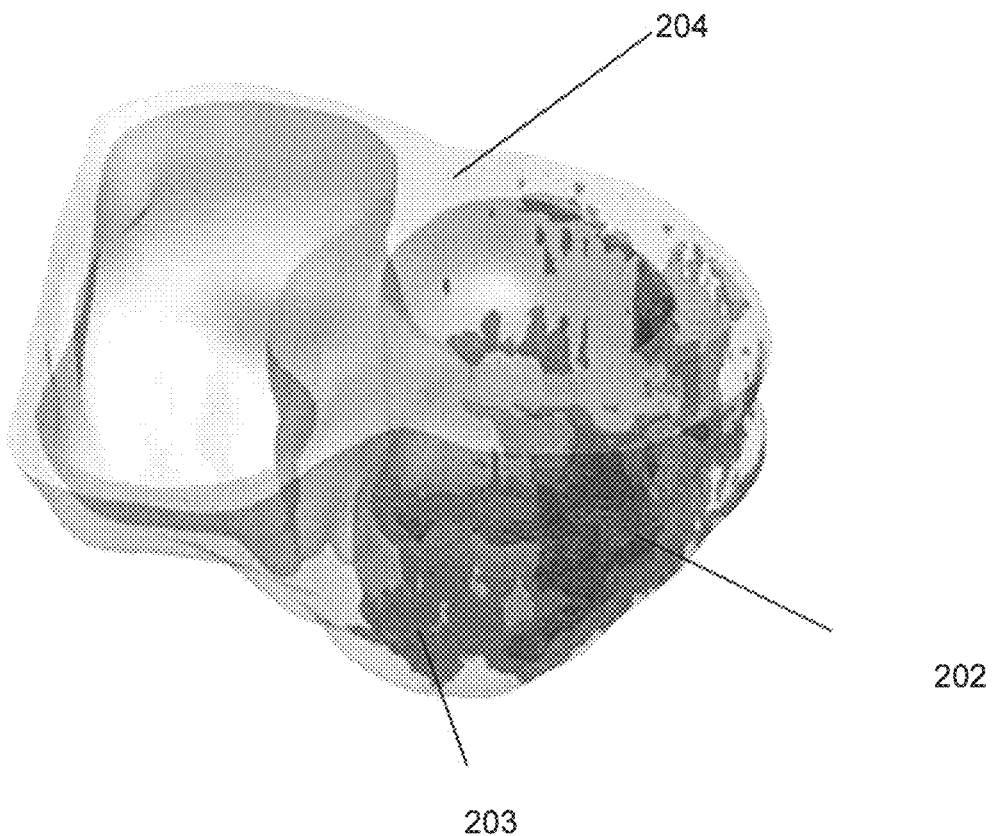

FIGS. 2a and 2b provide exemplary images of a heart 201 with identified cardiac tissue. FIG. 2a is an exemplary image of a heart 201 illustrating identified scar tissue 202. FIG. 2b is an exemplary image of heart 201 illustrating scar tissue 202, border zone tissue 203, and healthy tissue 204.

In some embodiments, heart 201, scar tissue 202, border zone tissue 203, and healthy tissue 204 may be displayed in a built-up format, which may provide physicians with an inside-out perspective of scar tissue. Empty space within the heart 201, e.g., the ventricles, may be displayed in a solid color. Scar tissue 202, border zone tissue 203, and healthy tissue 204 may then be displayed as built-up areas on the surface of the solid colored empty space. In such an embodiment, healthy tissue 204 may be displayed in a transparent fashion so that border zone tissue 203 and scar tissue 202 may be more readily visible. A built-up format representation of the heart may permit a physician to understand the identified cardiac tissue from an alternative perspective.

Returning now to FIG. 1, a user may next have the option of adjusting the segmentation, and user adjustment step 103. A user may adjust the cardiac tissue segmentation manually and/or may redo one or more of the above segmentation steps. The display may allow the user a variety of methods to evaluate the quality of the segmentation, including methods such as overlaying the segmentations over the raw pixel data, scrolling through segmented images, constructing, viewing and rotating isosurfaces of the segmented cardiac tissue types, and viewing voxel intensity images of the cardiac tissue. In addition to these visualizations, the segmentation display may show any scalar, vector, or tensor field in 2 or 3 dimensions by modifying hue, opacity, specular intensity, and material texture, or by introducing symbols overlaid with the or alongside the original images representing the same. Examples of such displays include displaying a hue gradient or voxel intensity rendering, partial opacity, vector fields represented by arrows where arrow size and color are scaled by another field, tensor fields represented by ellipses, and so on. Fields of interest include metrics representing the degree of confidence an automatic metric has in the quality of its segmentation, vector fields showing the evolution of a level-set algorithm, and differences in voxel intensity convoluted with the resulting segmentation.

In some embodiments, user segment adjustment may be automated or semi-automated. For example, shape analysis and other image processing may automatically or semi-automatically be performed on the scar and border zone, and used to tailor the processing of the images, including but not limited to flagging content for human review, suggesting that the patient has the "wrong" type of scarring for use of the ablation guidance system, suggesting possible diseases and etiologies that might have caused the scarring, (for example dispersed scarring in sarcoidosis) and alerting physicians to any life-threatening findings.

Figure 4:
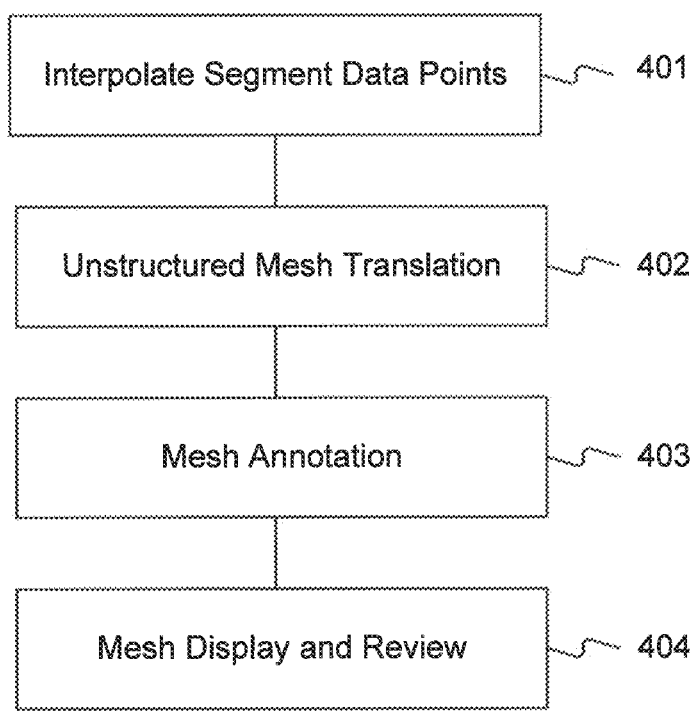
FIG. 4 is a flowchart illustrating steps in an exemplary model generation method.

At model generation step 104, a cardiac model may be generated based on the tissue identified during segmentation steps 102 and 103. Once the tissue has been segmented and all relevant cardiac tissue types have been identified, the raw image and segmentations may be converted into an unstructured finite mesh suitable for numerical solution analysis. FIG. 4 is a flowchart illustrating steps in a model generation method 400 corresponding to model generation step 104.

Raw images and their segmentations may be interpolated in space to create a new image having a finer resolution than the raw cardiac imaging data at interpolation step 401. A mesh having a higher resolution than the raw cardiac imaging data may permit simulations to run more smoothly. Interpolation may be done through a combination of methods, for example: variational implicit function fitting via thin plate splines, spherical harmonic interpolation, morphological expansion and erosion, optimizations of surface curvature, linear or cubic pixel interpolation, and other techniques known in the art. After a suitable resolution is achieved, either through interpolation or direct use of the cardiac imaging data, the identified cardiac tissue segments may be translated into an unstructured mesh.

At mesh translation step 402, the data points of the cardiac tissue segments are translated into an unstructured mesh. Exemplary methods that can be used to generate such an unstructured mesh include Delaunay Tetrahedralization, Almost Regular Delaunay Tetrahedralization, or voxel-based image meshing techniques After construction of the unstructured mesh, annotation of the mesh is provided at mesh annotation step 403. Ail or some mesh elements may be annotated during mesh annotation step 403. Mesh elements may be annotated with, for example, cardiac tissue type and muscle fiber orientation. Muscle fiber orientation may be expressed as a single unit vector (describing fiber orientation) and as a 3 dimensional orthogonal rotation describing fiber, laminar, and sheet transverse orientations within the tissue. The fiber orientation may be derived from fully automated methods (such as Laplace-based rule filters) or from semi-automatic methods such as using large-scale nonlinear deformations to deform an atlas image with fiber orientations to the patient's specific geometry.

Once the annotated mesh has been constructed, the resulting mesh can be presented to the clinician for review at mesh display and review step 404. The visualization may allow the operator to visualize the resulting mesh, isosurfaces of all the segmented tissue types in the original image, streamtracing of the resulting fiber orientation, and overlay this data on top of the original mesh and segmentations. During mesh display and review step 404, a user may determine whether the annotated mesh is satisfactory. A user may decide that any of the previous steps must be performed again, and may decide that such repetition be performed on only portions of the annotated mesh. For example, if a user decides that only a portion of the annotated mesh is unsatisfactory, the user may decide to resegment only that portion. In some embodiments, mesh display and review step 404 may be fully or semi-automated. The processing machine may be programmed to carry out instructions to perform the annotated mesh review automatically or with various levels of user guidance.

Returning now to FIG. 1, the annotated mesh generated in cardiac model generation step 104 represents a cardiac model. The cardiac model contains information about scar tissue and cardiac fiber orientation. The cardiac model may be used to simulate electromechanical operation of the heart.

At stimulation protocol simulation step 105, a user may employ the cardiac model to simulate cardiac activity. Cardiac activity may be simulated through the use of stimulation protocols.

First, the user may create one or more stimulation protocols intended to induce VT in the cardiac model. A stimulation protocol includes at least one model stimulation site, i.e., a point or points in the heart where a stimulus or stimuli will be applied, and start times and duration of the stimulus at each stimulation site. The model stimulation sites may be selected to permit the model to simulate a cardiac disorder, such as VT or AF. Protocols may either be created automatically, semi-automatically, or manually. If a protocol is created automatically, relevant stimulation protocols to induce VT may be chosen based on an atlas heart, and those points and times are transformed to the individual patient's heart. If a protocol is created manually, the user may design the protocol using an interface that permits the selection of stimulation locations and times. If a protocol is created semi-automatically, some combination of user input and atlas-transformed preprogrammed stimulation protocols are used to design the stimulation protocols.

The annotated mesh and stimulation protocols may then be simulated using any suitable analysis technique, for example, finite-element, finite volume, and/or finite difference. The simulation may rely on the bidomain or monodomain equations. The bidomain equations are a mathematical representation of cardiac electrical properties. The monodomain equations are a simplified version of the bidomain equations. Throughout the mesh, specific cardiac electrophysiological properties are used during the simulation, including changes to fiber, sheet, and laminar conductivities, cell membrane capacitance, and surface/volume ratios, membrane currents, and membrane dynamics on a tissue-type/point-to-point basis. Prior to simulation, stimulation protocols may be analyzed to minimize the necessary computation. In some embodiments, each stimulation protocol may be simulated naively, with no additional knowledge of previous simulation runs, while in others, the state of the simulation for one stimulation protocol may be saved to storage at a time where it diverges from another stimulation protocol, and the resulting time-evolution up until that point may be shared by both stimulation protocols.

Simulations may be run either directly on the processing machine, in which case the annotated mesh may be already available either in memory or disk of the processing machine, or the simulations may be offloaded to a remote cluster to speed processing time. In the event of the latter, the annotated meshes and stimulation protocols may be transferred via a HIPAA-compliant file-sharing service, ssh/scp, rsync, Bittorrent Sync, or other suitable transfer method.

Figure 5:
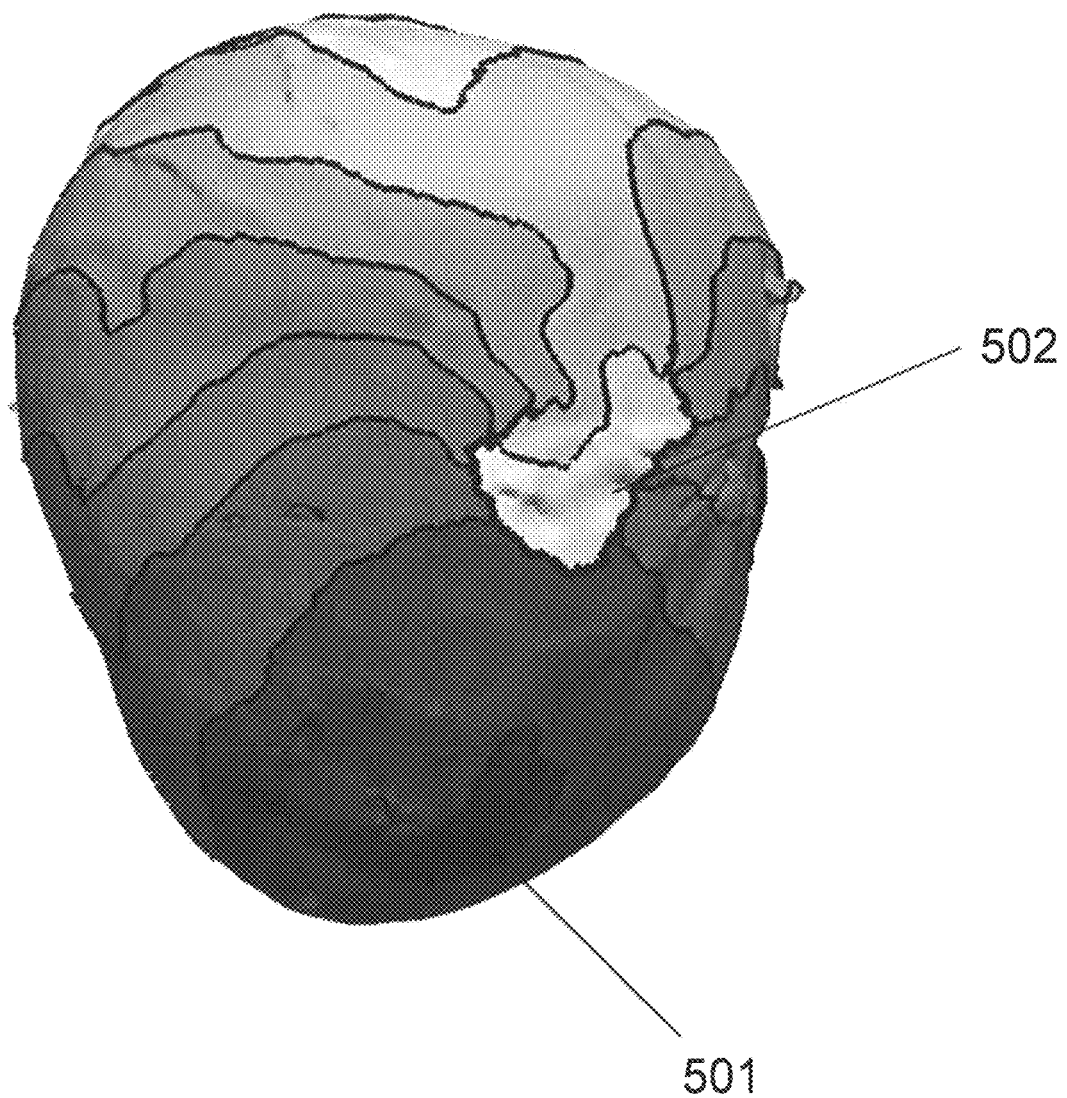
FIG. 5 illustrates an exemplary simulation output, an activation map of the heart, displaying a time progression of activated cardiac tissue.

Each simulation may produce a variety of outputs, including, for example, an evolution of the simulated transmembrane voltage over time in the mesh, simulated ECG activity, activation times and thresholds, activation maps, time-evolution of individual or gross membrane currents, and any other quantities simulated during the duration of the simulation. FIG. 5 illustrates an exemplary simulation output, an activation map 500 of the heart, displaying a time progression of activated cardiac tissue. As illustrated in FIG. 5, cardiac activation progresses from the darkest areas to the lightest areas. The activation map 500 of FIG. 5 reveals an arrhythmia at tissue region 502. An activation wave beginning at tissue region 501 progresses to each succeedingly lighter tissue region. As shown in FIG. 5, the activation wave splits and wraps around tissue region 502 before returning to tissue region 502. Once tissue region 502 is activated, the wave may then continue and reactivate the darker tissue regions again. This type of reentrant arrhythmia may continue in this pattern indefinitely, irrespective of the heart's natural sinus rhythm. In this example, ablation treatment at tissue region 502 may serve to prevent reentry of the activation wave, eliminating the associated arrhythmia.

Treatment target location step 106 may use data from stimulation simulation protocol step 105 to locate cardiac targets. Cardiac treatment targets may be identified such that, when treated in the cardiac model, the cardiac activity simulation may be altered. For example, after simulated treatment of an identified target, simulated VT occurring as a result of a certain stimulation protocol may be reduced or diminished. Target identification may occur during or after stimulation protocol step 105 has finished. Actual treatment of cardiac treatment targets in the patient's heart is thus expected to produce the same or similar results to simulated treatment of cardiac treatment targets. That is, based on the model simulation, it is expected that actual treatment of a patient's heart in a location corresponding to the cardiac treatment target will reduce or diminish the potential for VT in that patient.

The simulation may produce data pertaining, for example, to membrane voltage distributions, tissue displacements, ion concentrations, and more. Membrane voltage distributions may include maps of intracellular, extracellular, and/or transmembrane potentials throughout the heart and/or on the surface. Tissue displacement data may include, for example, an amount of movement of each portion of the tissue from a reference position, e.g., rest (diastole) to an expanded position, e.g., with the ventricles full of blood. Ion concentration data may include, for example, extracellular, intracellular, and sarcoplasmic reticulum ionic concentrations of Na+, Ca++, Cl−, K+, and other relevant ions. These data may be processed into a variety of process metrics that a clinician may find useful. These metrics may include any and all relevant phenomena that may be derived with the simulation data.

For example, process metrics may include, activation maps, also known as isochrones. Activation maps plot the location of the propagating wavefront at different times, where the wavefront may be identified based on a maximum rate of change of voltage (e.g., 8 mV/ms) and an absolute voltage threshold (e.g., −40 mV). Activation times may be displayed in an activation map either continuously (e.g., by color gradient) or discretely (e.g., by lines or colored regions that change every 1 ms or 10 s for example.

Process metrics may further include simulated 12 lead ECG traces. Electrical data from the simulation model may be used to simulate the output from a standard 12 lead ECG trace. That is, the model may determine that the electrical propagation data, if occurring in an actual heart, would produce a certain ECG trace if measured by a conventional 12 lead ECG measurement method. This may provide a physician a data format which they are familiar with and accustomed to reading.

Process metrics may further include the locations of late potentials during sinus rhythm. Late potential locations may be understood in a manner similar to an activation map, except that only late activation times, e.g., activation occurring after the propagation wavefront has passed, are included.

Process metrics may further include simulated recreations of what a catheter will record if placed in a given location. Sensing catheters may record electrograms (EGMs) on endocardial or epicardial surfaces of the heart. Recorded electrograms may have a distinct appearance that varies depending based upon what type of catheter is used, i.e., unipolar, bipolar, or multipolar catheters. Electrograms may also be recorded by pacemakers and defibrillators using their leads. Electrograms may be simulated by passing the transmembrane or extracellular potentials in a simulation model through filters and sampling sites meant to mimic the physics of commonly used recording catheters and leads. Thus, the system may produce simulated EGMs in a format familiar to physicians.

Process metrics may further include maps of action potential phases. Action potentials in cells pass through several phases—a rising phase, a peak phase, a falling phase, an undershoot phase, and a refractory phase. Maps of action potential phases may illustrate in which phase various cardiac cells are in at a given time. Such maps may be produced for a single moment in time, or for a progression or time sequence.

Process metrics may further include locations and time courses of arrhythmic points and/or arrhythmic filaments during a simulation. Marking arrhythmic points and or filaments may illustrate an organizing center of a re-entrant wave of activation which may lead to a tachycardic rhythm. The center of a spiral propagation wave has a phase singularity. That is, it has a phase that does not match a defined phase of action potential associated with cardiac electrical waves, because it is constantly having current fed in and drawn by the various parts of the cardiac activation sequence that surround it. These centers are considered to be organizing centers of re-entrant cardiac activity. In two dimensions, this yields an arrhythmic point. In three dimensions, e.g., with a scroll wave, a spiral wave extruded into an extra dimension, there is a line of arrhythmic points in the direction of extrusion. This line may be an arrhythmic filament. By marking these points and/or filaments, it is possible to illustrate the organizing center of a re-entrant wave of activation in the heart.

Process metrics may further include overlays of subsequent sinus beats to detect abnormally refractive regions. Cardiac cells have a refractory period during which cells recharge for the next action potential. If a refractory period is longer in one region than in another, for example, due to an ischemia, then that region may fail to activate during every heartbeat, as it cannot activate at the same rate as the surrounding tissue. Thus, an abnormally refractive region may miss one or more beats of activation. Abnormally refractive regions may lead to unidirectional block and therefore creation of reentry.

Process metrics may further include the movement of the tissue and ejection dynamics for simulated data. Computational fluid dynamics, combined with tissue motion as described above, may be used to estimate an amount of blood ejected from the left ventricle with each contraction of the heart. This is an important clinical metric used to quantify how well the heart is performing as a pump, and is known as left-ventricular ejection fraction (LVEF). The motion of the blood may be illustrated using vectors (arrows of various sizes and directions), moving particles, or simply a graph showing the blood flow through the aortic valve with each contraction.

Process metrics may further include propagation dynamics, such as conduction velocity or channel width. Conduction velocity may be calculated from data similar to that used to produce activation maps. Conduction velocity may be calculated as an average, e.g., a velocity of signal propagation from one point to another distant point, and as a discrete measure, e.g., a velocity of signal propagation between two adjacent nodes in the mesh. Channel width may be understood as a width of a channel through which a signal wavefront propagates. For example, if the signal wavefront is viewed as a surface that moves through space, its path can be used to create a tunnel or channel, extruded as the wavefront moves. The width of this channel may illustrate "critical pathways," which may be blocked with a small number of ablation lesions. A channel may be display in a still image, a wavefront over time may be displayed in an animation, or the system may simply highlight locations where the width of the tunnel or channel is of a certain size, with or without numerical callouts indicating the size.

One or more of the above metrics may be used by an automated or semi-automated process to identify treatment targets for ablation therapy. In some embodiments, a clinician may be given a choice from a predefined list of methods to select locations for ablation therapy. In other embodiments, a clinically validated algorithm may be applied automatically for the clinician. In still other embodiments, the clinician may be avowed to program a new algorithm for selecting ablation locations. Examples of these targeted location selection algorithms may include selecting target locations based on the threshold of the accumulated distribution of phase filament locations over time, or selecting target locations based on minimal channel widths that sustain arrhythmic propagation.

Figure 6:
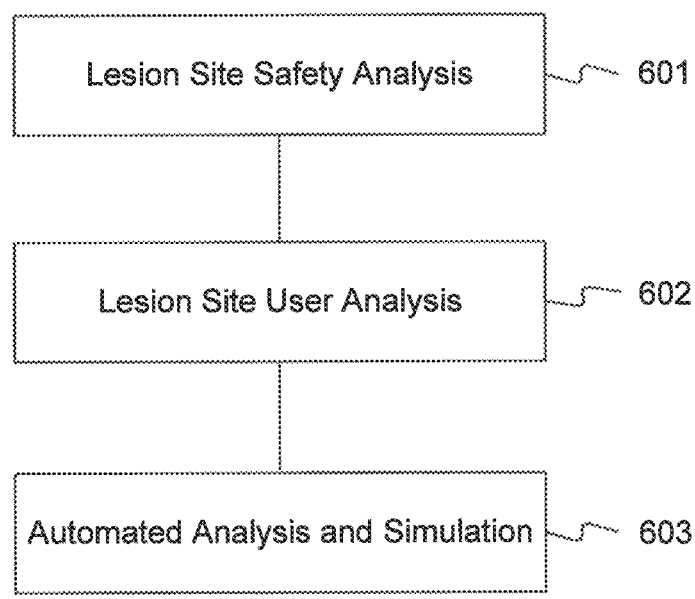
FIG. 6 is a flowchart illustrating steps in a target processing method.

Following the selection of treatment targets at treatment target identification at step 106, identified treatment targets may be subjected to post-processing, at treatment target processing step 107. Treatment target processing step may be performed after the completion of treatment target identification step 106, or concurrently as treatment targets are identified. Treatment target processing step 107 is illustrated in further detail in FIG. 6, which is a flowchart illustrating steps in treatment target processing method 600.

Figure 7:
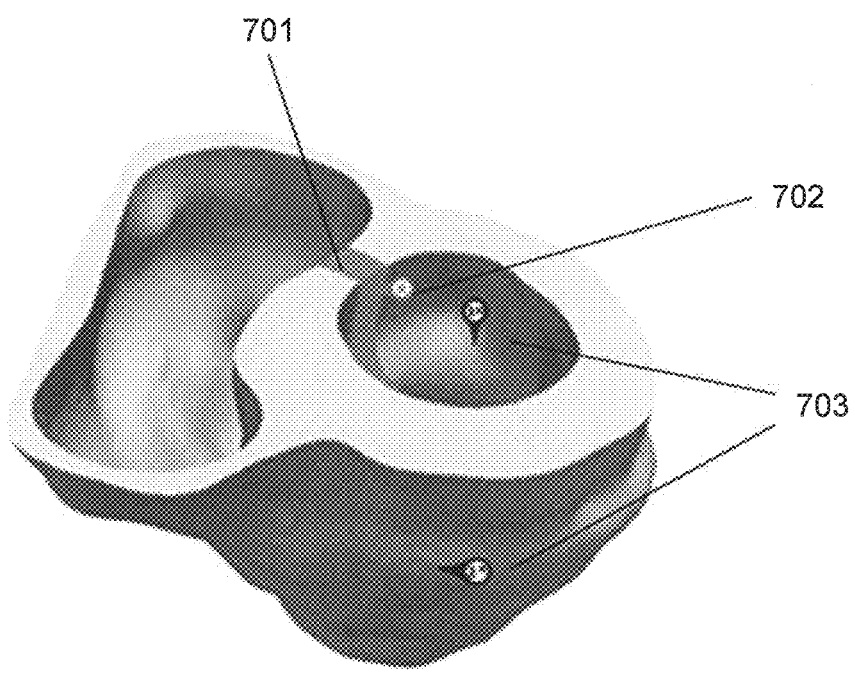
FIG. 7 illustrates an exemplary treatment target safety analysis image.

Identified treatment targets may be analyzed for safety during lesion site safety analysis step 601. FIG. 7 illustrates an exemplary treatment target safety analysis image 700, identifying high-risk region 701, high-risk treatment target 702 located within region 701, and low risk treatment targets 703. During lesion site safety analysis step 601, the clinical safety of treatment targets may be examined. In some embodiments, a predefined atlas of regions considered high-risk for lesion placement may be stretched and registered to the cardiac model containing identified treatment targets, using either automatic or manual registration methods. Exemplary methods to perform a stretching/registration process may include a simple affine transformation based on a least squares regression of the best fit from a number of manually selected common points, diffeomorphic mappings such as LDDMM, and a parameterization of the ventricular tissue. Lesion site analysis step 601 may assign risk factors and/or success likelihood factors to each identified treatment target for display to a user. Success likelihood factors may identify, for example, on a percentage basis, how likely a lesion placed at the associated location is to reduce or diminish disordered cardiac activity.

Should a risk or success likelihood factor exceed a certain predefined threshold, the associated treatment target may either be eliminated from the list of treatment targets, after which testing alternate targets may be identified, or it may be marked to indicate to the operating physician that the site is considered a safety risk or has a low success rate and should be treated with care. In some embodiments, during lesion site safety analysis step 601, a plurality of initially identified treatment target sites may be assessed based on risk and success factors, and an optimal subset of the identified treatment target sites may be selected for further analysis.

Lesion site safety analysis step 601 may also be completed using an atlas of difficult-to-access regions. Difficult-to-access regions may include, for example, a preference for endocardial sites over epicardial sites, right ventricle access to the septum rather than left ventricle access to the septum, indications for trans-septal ablation with two catheters, and avoidance of large papillary muscles. Lesion site safety analysis step may also account for safety and access parameters of different models of catheters, and/or different types of catheters, factoring in lesion size, safe lesion depth, lesion shape, flexibility of the catheter, stiffness of the catheter, presence or absence of force sensing, presence or absence of integrated ultrasound imaging, and presence or absence of other sensing and imaging modalities. Lesion site safety analysis step 601 may further be used to recommend specific catheters for the best lesion placement or safest approach by comparing the success of simulated lesions placed within the different sets of safety and accessibility constraints associated with each catheter type. In some embodiments, a user may select between all optimal targets, which may include both epicardial and endocardial locations, and targets by approach, which may be limited to either epicardial or endocardial locations. If, for example, an endocardial approach is selected, only endocardial targets will be displayed for the user and alternative endocardial sites may be substituted for epicardial sites.

In some embodiments, it may be recognized during lesion site safety analysis step 601 that multiple lesions may be required to fully ablate an identified target. In such a case, analysis step 601 may identify location groups, each including one or more cardiac treatment targets selected to ablate an identified target region.

In some embodiments, lesion site safety analysis step 601 may present alternative treatment targets to an operator as the initial treatment targets are viewed. For example, when presented with a series of primary treatment targets, a user may select an individual primary treatment target and view possible alternative treatment target locations. Alternative treatment target locations may be determined so as to have a similar effect on a patient's VT as a primary target location. Thus, if an operator determines that a particular target location among the primary target locations is unsafe, that operator may then select the particular target location and immediately be presented with a selection of alternative target locations that, if ablated, may have a similar effect to ablation of the primary target location.

Following safety analysis, lesion site user analysis step 602 may be conducted to receive a user's input. A user may make custom maps either preferring or avoiding certain lesion sites, by marking such locations on a generic atlas heart, by marking such locations on the patient's medical images used for mesh generation, or by providing any other indication to the system of locations that the user would prefer to use or avoid. In some embodiments, a plurality of potential targets may be displayed, including redundant locations. As a user selects target locations for therapy, the displayed target locations may be dynamically altered based on the users selection. For example, where the simulation has determined that a lesion placed in a first location would obviate the need for a lesion in a second location, the second lesion location may be removed after the first is selected.

In some patients, a pattern of cardiac scar tissue may have the potential to give rise to multiple VT patterns. Although there may be the potential for multiple VT patterns, in some patients, a single VT pattern from among the multiple patterns may be more likely to actually occur. Such VT patterns may give rise to clinical, observable VT rhythms. In some embodiments, the system may identify which from among the identified treatment targets contribute to clinical VT as observed by a physician. A physician may collect data related to a clinical VT, for example, by ECG or other detection method. Such data may include, for example, cycle length of an observed VT. Inputting data related to an observed VT may permit the system to identify treatment targets that may correspond to or contribute to the clinical VT.

In some embodiments, when selecting target locations for therapy, a user may prioritize or rank the locations. For example, a user may select a specific order in which locations should be targeted for ablation. In other embodiments, a user may provide specific rankings, e.g., on a 1-10 scale, of how important the target location is for ablative therapy. Automated analysis and simulation step 603 may be conducted after the lesion sites have been finalized. A clinician may optionally choose to re-run the simulation protocols to examine if the given lesions terminate arrhythmia within the simulation. During automated analysis and simulation step 603, a user may instruct the system to update the cardiac model based on the expected treatment of one or more of the identified target treatment sites and resimulate cardiac activity based on the updated model. The model may also be updated based on an expected outcome of treatment, where the expected outcome is based on a mode of treatment or device used for treatment. Predictions of expected outcomes are explained in greater detail below. A user may further iterate between designating ablation sites and visualizing the simulated effects of those ablation sites until they feel satisfied with the result. Changes to treatment targets may be marked in maps provided to the clinician, or left out of the information shown to the clinician. A user may set a threshold to limit the number of attempts to re-simulate the patient's heart iteratively in this process, based on, for example, clock time, computational cost, or number of attempts.

Returning now to FIG. 1, the finalized selection of target treatment sites may be exported in target map export step 108. Target map export step 108 may export target map data. Target map data may be exported to a storage location for later use, such as a central database located on a server, or may be exported directly to a cardiac therapy system, which may include a cardiac mapping and navigation system and/or a cardiac ablation system. In some embodiments, a cardiac therapy system as disclosed herein does not include either a cardiac mapping and navigation system or a cardiac ablation system, but includes an ability to interact with one or more of these systems. In some embodiments, target map data may be exported to multiple locations at once. In some embodiments, exportation of target map data refers only to an export of the data from one aspect of a processing machine to a second aspect of a processing machine. For example, after generating a target map data using a cardiac mapping system, a user may export the target map data and transition to use using the target map data with the cardiac mapping system to locate designated target sites within the patient's heart in a clinical setting, outside the model. Target map data may be exported by any suitable means, including but not limited to transfer via flash disk, hard drive, optical disk, network connection, or PACS. Target map data may include any or all of the finite element cardiac model, simulation data, and selected lesion sites. Target map data may provide the data required to display treatment targets to a user, and may provide the data required to locate treatment targets in the heart of the patient.

Figure 8:
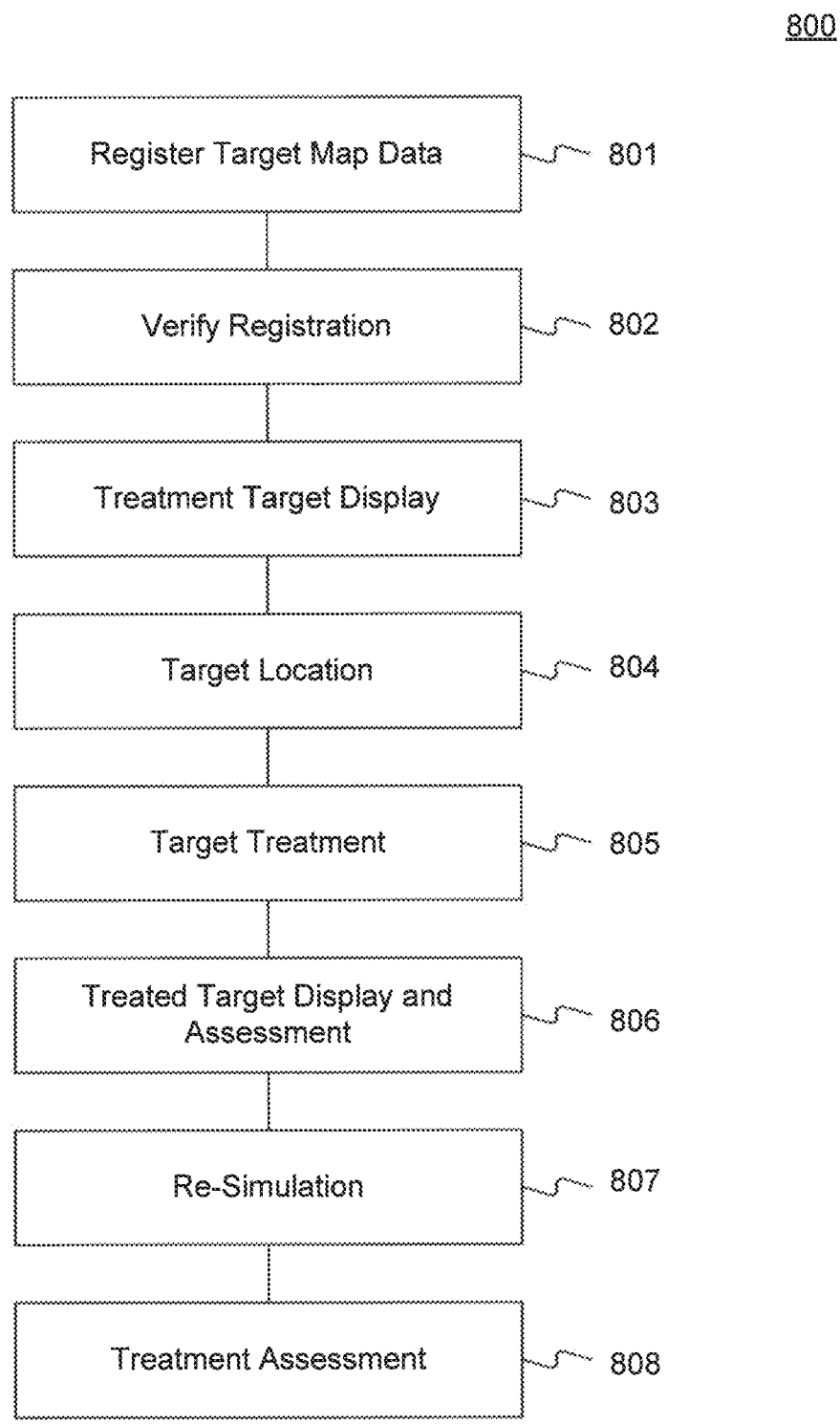
FIG. 8 is a flowchart showing an exemplary target treatment method.

FIG. 8 is a flowchart showing exemplary target treatment method 800. Target treatment method 800 may be performed after the target map data is produced and exported.

Target treatment method 800 may begin with target map data registration step 801, the target map data is registered to navigational data for a cardiac treatment device, such as an ablation catheter. Once registered, the target map data and navigational map data may be combined into a fused map. The target map data contains information about the patient's heart, for example, target sites for treatment. This data must be made to correspond to navigational data of that patient's heart in the actual clinical setting, so that the EP can accurately guide a catheter or other treatment device to the target treatment devices determined via the cardiac simulations.

Figure 3:
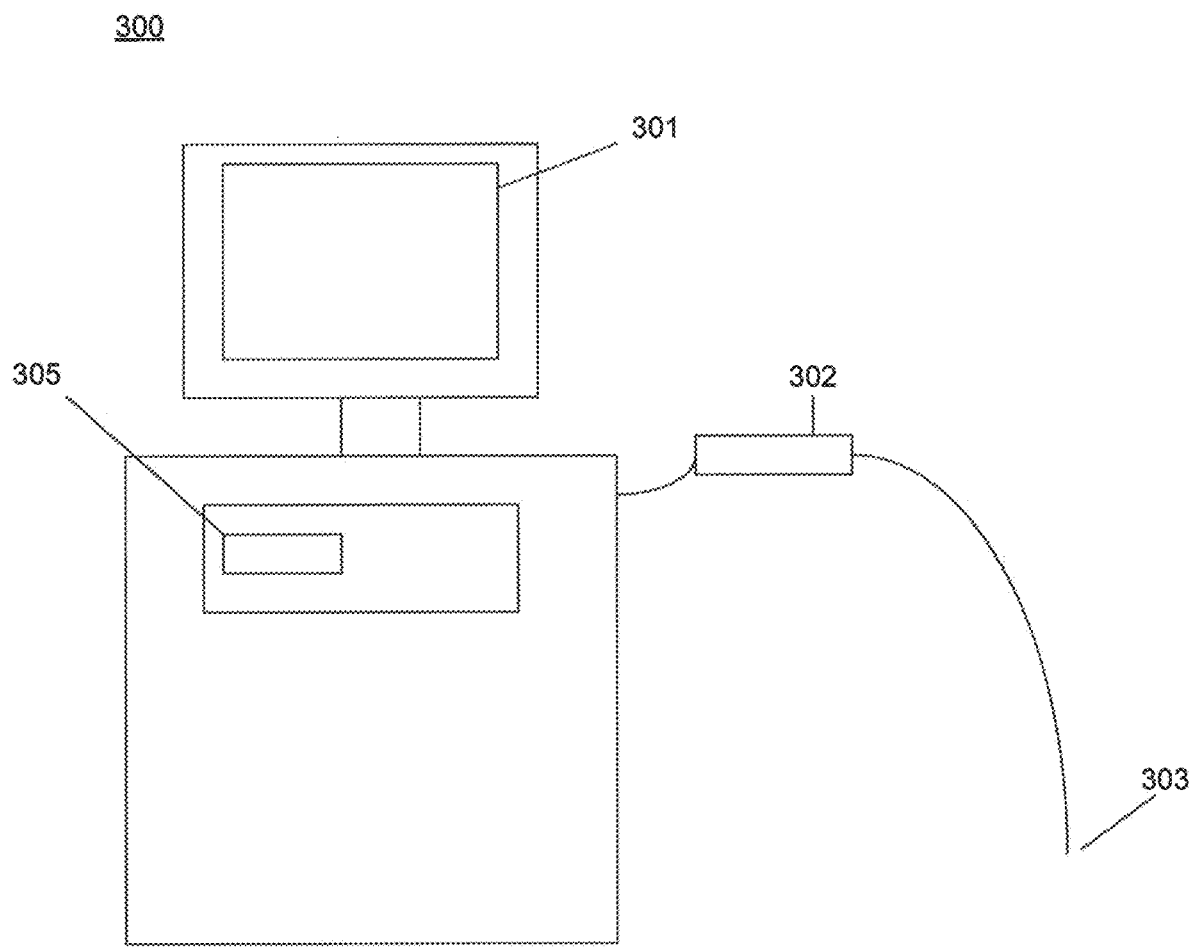
FIG. 3 illustrates exemplary components of a cardiac mapping and navigation system.

Some embodiments of the present disclosure may make use of a cardiac mapping and navigation system to facilitate target map data registration step 801. FIG. 3 illustrates exemplary components of cardiac mapping and navigation system 300. Cardiac mapping and navigation system 300 may include mapping catheter 302 having a mapping tip 303. Cardiac mapping and navigation system 300 may further include display 301 and a processing device 305. Processing device 305 may be configured as described herein to perform various steps of the methods described.

Display 301 may include, for example, basic displays such as computer monitors or televisions connected to computers or cameras. Display 301 may also include virtual and/or augmented reality glasses or other wearable displays, including, but not limited to Google Glass, Oculus Rift, Samsung GearVR, Google Cardboard, and Microsoft HoloLens. In embodiments including a wearable display, cardiac mapping images may be projected onto a physician's glasses as they perform a procedure. Such images may be projected to overlay on the actual patient, permitting the physician to see the cardiac mapping and navigation system display 301 without turning attention away from the patient. Implemented as a wearable display, display 301 may also permit a physician to manipulate and rotate navigation system 300 images through head movement, permitting the physician's hands to remain free to operate a catheter.

Novel visualizations may be produced using such wearable systems, including 3D fly-throughs, synchronization of the simulation data, and/or model of the clinical ECG allowing projections of a beating heart image appearing to be in or hovering over the patient's chest, display of any of the metrics or visualizations mentioned herein on such a visualization, visualization of the position of the catheter within the 3D model of the heart and/or the patient's other vasculature, visual cues such as warnings or indications that a target location has been reached or of the amount of ablation energy applied relative to effective and dangerous thresholds via flashing of the display, virtual floating objects showing distance, a "blown-up" or "zoomed-in" visualization of the components of the ablation system and model relative to one another (for example, the heart's dimensions expanding to show the model eight-feet wide floating over the patient as the catheter closes in on an ablation target), red tinting of the display if a dangerous area is being approached by the catheter, or tunnel vision (blocking out the periphery) to enhance focus on a target region as it is approached. Changes in visual (3D) focus or distance of the illustrations shown on display 301 may be used to convey distance between objects or indicate other metrics as described above.

A wearable embodiment of display 301 may be controlled by many methods, including but not limited to computer vision to track the patient/hands/equipment in the lab, sensor gloves, reflective markers with a laser illuminator, vocal commands by the physician, a gamepad or joystick, or keyboard and mouse controls.

Cardiac mapping and navigation system 300 may include, for example, the CARTO™ system by Johnson & Johnson or EnSite™ NAVX™ by St. Jude Medical. Cardiac mapping and navigation systems 300 provide to a clinician the ability to map cardiac electrical potentials via a catheter inserted into the heart. Cardiac mapping systems 300 monitor the spatial location of catheter mapping tip 303 after it is placed inside a patient's heart, for example through the use of magnetic fields. A location of catheter mapping tip 303 may be displayed with respect to cardiac anatomy on display 301. Electrodes on the catheter tip 303 may be placed against the cardiac wall and used to measure electrical potential in the cardiac tissue throughout a cardiac cycle. By taking multiple electrical readings and combining these with data about the location of the catheter tip 303, an electrical potential map of the heart may be created. In some embodiments, electrical readings are not required, and a physical map of the heart may be built simply by recording the location of the catheter tip 303 as it is moved through the interior of the heart.

AH or some of the previous steps may be carried out on a cardiac mapping and navigation system 300. For example, the cardiac mapping and navigation system 300 may include at least one processing device 305 configured to carry out instructions to perform the model building and simulation steps described above. In other embodiments, model building, simulation, and target map generation may be performed separately, and the target map may be imported to the cardiac mapping and navigation system 300 in order. To enable this import, the target map data may be rendered in a format suitable for import to the corresponding mapping system, such as a DICOM image, a VTK mesh file, or other appropriate format. The resulting file may then be loaded onto the meshing system by a network interface on the mapping system itself, a USB flash drive, or a CD/DVD ROM disc. The network interface may be used to access a PACS server, local to the clinical environment Several techniques may be used to register the target map data with a navigation map. In some embodiments, registration may be performed simultaneously to mapping. For example, a clinician may guide a catheter tip to a specific location within the heart, for example, the apex, and may record this location in the mapping system at the same time as instructing the mapping system to correlate the newly mapped location with an apex location in the target map data. This process may continue, locating areas of the patient's heart with the catheter tip and correlating them to locations in the target map data.

In other embodiments, a navigational map is generated prior to registration. A clinician may use a mapping catheter to generate a navigational map of the heart, and then, using the mapping system, designate correspondences between the navigational map and the target map. This type of registration may be performed manually by permitting a user to manipulate the images via a user Interface on the display of the cardiac mapping and navigation system 300. Alternatively the registration may be performed in an automated fashion by the cardiac mapping and navigation system 300. The target map data may include markers to assist with the fusion. Such markers may be anatomical in nature, e.g., the right-ventricular outflow tract, the middle of the interventricular septum, the apexes of one or both ventricles, the borders of the ventricular valves, or existing implanted hardware.

In some embodiments, additional registration methods may include automatic integration with existing registration markers in a cardiac mapping and navigation system 300, automatic fitting to scar maps created during the ablation procedure, automatic fitting to other measurements made during the ablation procedure, integration with live imaging (echo, MRI, CT, fluoroscopy), and/or integration with other fiduciary markers such as those integrated in the Mediguide™ system.

In some embodiments, target map data may be registered to other heart models used for the navigation of the ablation catheter, including but not limited to models created by CartoMerge and the endocardial surface maps created by the mapping and navigation system(s).

After completion of an initial registration in target map data registration step 801, registration verification step 802 may be performed. During registration verification step 802, mapping of the scar regions may be done to verify the registration as well as scar shape and location. A mapping catheter may be advanced to the location of scar tissue as identified by the fused map. This area may be electrically mapped and to ensure that these areas are indeed scar tissue. Thus, the registration may be verified and the fused map data confirmed. If the tissue that is mapped shows not to be scar tissue, but, for example, border zone tissue or healthy heart tissue, then a user can attempt to automatically refuse the images. Alternatively if the shape, size, or location of the fused map scar region does not match the electrically mapped region, the user may manually alter the target treatment map data to match the empirical results taken via electrical mapping.

The user may be provided a user interface on the display of the cardiac mapping and navigation system 300 allowing the user to manipulate the target map data in ways including but not limited to translation, rotation, stretching, shrinking, morphing and skew. In some embodiments, target locations may be altered based on the inputs of the user. After the user has completed alterations to the target map data to better fit the navigational map data, stimulation protocol simulation step 105 may be performed against, using the altered data. The simulations, or a subset of the simulations, may be rerun to confirm that the altered target locations may still provide effective treatment.

In some embodiments, a user interface (UI) of the system may show both the original and new target locations. The UI may distinguish between the new and the old target locations by one of color, intensity, hue, transparency, or other methods. The target locations may also be labeled with words, numbers or symbols.

Figure 9A:
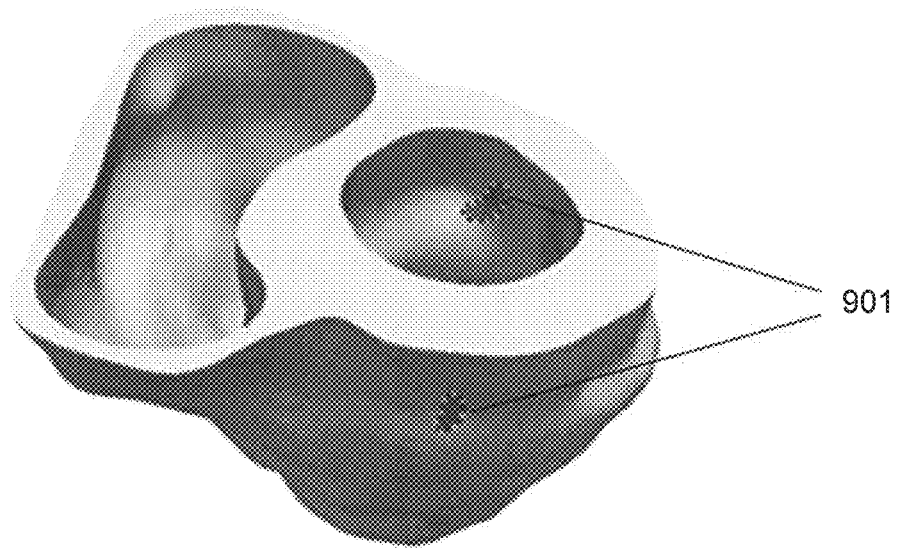
FIG. 9a illustrates a fused map with target sites shown as outlines.
Figure 9B:
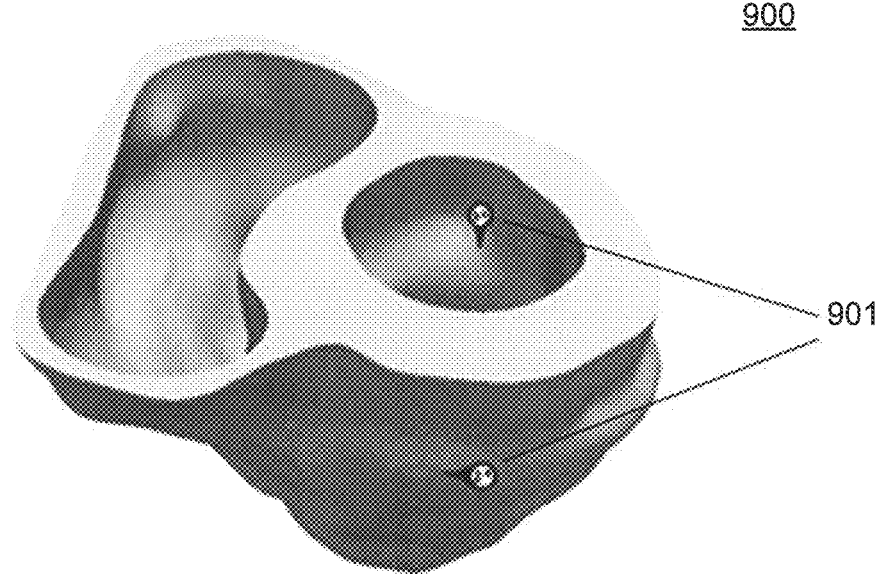
FIG. 9b illustrates a fused map with target sites tagged with text markers.
Figure 9C:
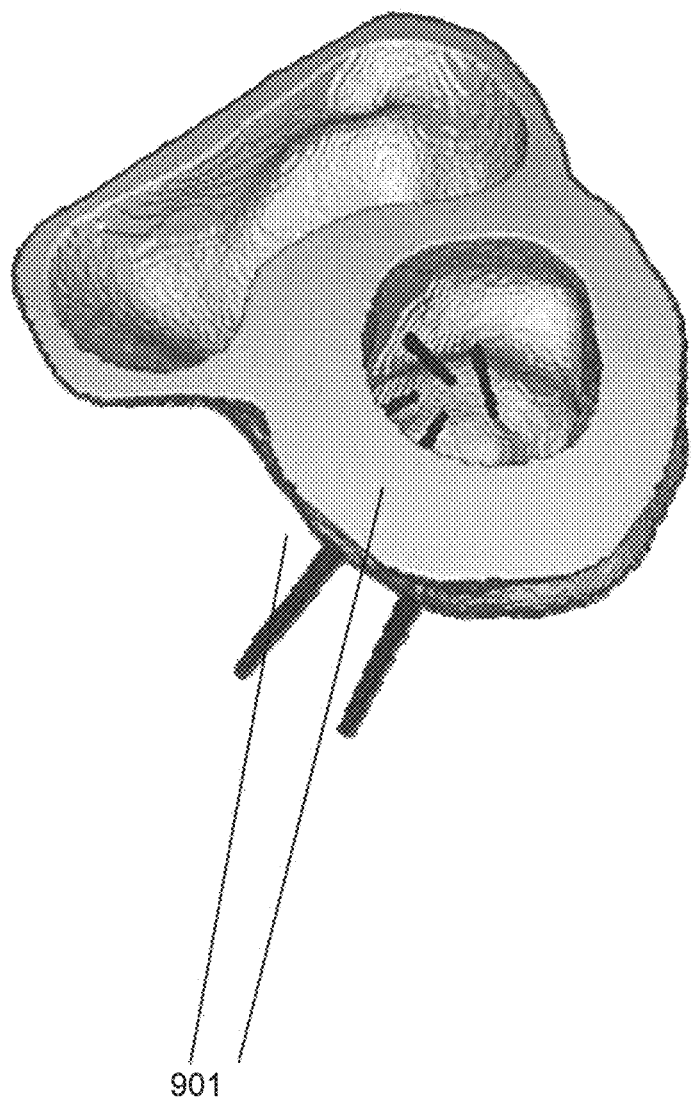
FIG. 9c illustrates a fused map with target sites marked with spires.

After registration has been verified and the fused map confirmed at registration verification step 802, the fused map may be displayed at treatment target display step 803. The treatment target sites may be displayed in a variety of different ways. FIGS. 9a-9c illustrate some exemplary modes of display.

Figure 9D:
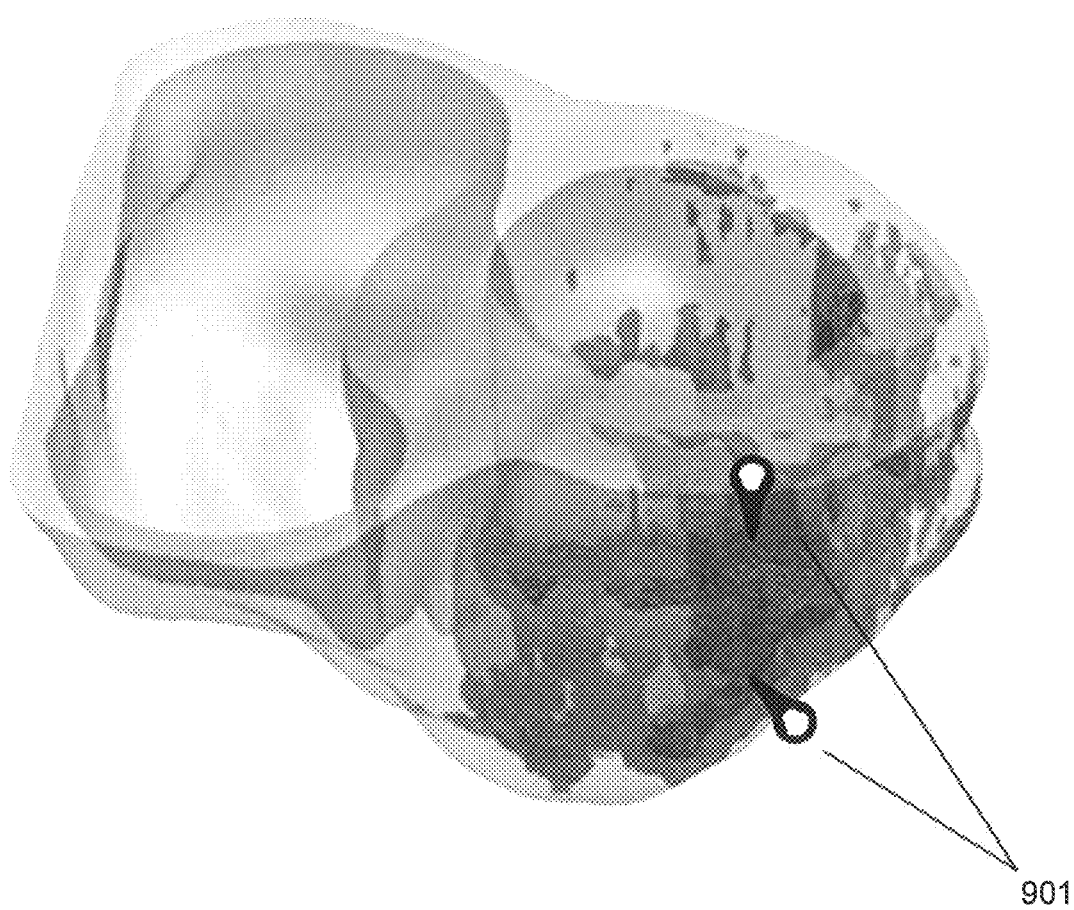
FIG. 9d illustrates a fused map with target sites marked with text markers, provided with a tissue zone overlay.

FIG. 9a illustrates a fused map 900 with treatment target sites 901 shown as outlines. FIG. 9b illustrates a fused map 900 with treatment target sites 901 tagged with text markers. FIG. 9c illustrates a fused map 900 with treatment target sites 901 marked with spires. FIG. 9d illustrates a fused map 900 with treatment target sites 901 tagged with text markers, and an overlay of identified tissue zones. This overly may permit a user to understand how potential lesion placement and identified tissue zones coincide.

Other methods of display may include a single point or a cluster of points for each treatment target site 901. Each may be displayed on the surface of the heart model, or may be a cylinder that extends through the entire thickness of the wall of the tissue of the heart. The treatment target sites 901 may be displayed as a different color than the heart tissue, scar tissue or border zone tissue that is displayed. The treatment target sites 901 may also be shown as the same color as one of the listed heart tissues but by altering at least one imaging properties such as color, hue, transparency, opacity, or vibrancy, or adding a rendered lighting effect such as a glow or an animated border. Alternatively, the treatment target sites 901 may be displayed as a spire that extends from the heart. In some embodiments, the spire may extend in the direction of the suggested ablation. If the ablation is recommended epicardially, then the spire will be protruding away from the heart or epicardially. If ablation is recommended endocardially then the spire will be protruding into the heart or endocardially. Alternatively, the spire may penetrate though both sides of the heart and be shown protruding from both the epicardial and endocardial surfaces of the heart to make viewing of treatment target site 901 area easier to see regardless of the view that is being displayed.

In other embodiments, the treatment target sites 901 may be displayed as gradients giving the user a general area for ablation instead of a definitive spot for ablation. This gradient may be arbitrary or changing in a predefined manner including linear, exponential decay, created per custom linear mapping by the end user.

In other embodiments, treatment target sites 901 may be displayed as a series of concentric rings. In some embodiments, progressively larger concentric rings may represent increased probability of ablation success if the ablation lesion envelopes that ring. Due to potential errors in registration and catheter location, a clinician may be unable to precisely locate an ablation catheter tip at treatment target site 901. Thus, an ablation lesion may have a greater chance of successfully treating the treatment target site 901 if it is large enough to ablate surrounding tissue. A series of increasingly larger concentric rings may be sized based on these potential errors, and used to convey to an operator information about how the probability of ablation success corresponds to lesion size. If the potential errors associated with the equipment being used are small, a smaller lesion may have a higher probability of success, and the size of the concentric rings would increase in relatively small amounts. If the potential errors associated with the equipment being used are large, a larger lesion may be required to have a high probability of success, and the size of the concentric rings would increase by relatively larger amounts. This type of display may facilitate the use of different mapping, navigation, and ablation equipment with the systems and methods disclosed herein.

Treatment target sites 901 may be displayed in conjunction with other features of the fused map 901, including but not limited to the scar tissue, border zone tissue, activation maps, conduction pathways, resting membrane potential, local conduction velocity, activation delay, block lines, or a movie of activation. Any of these may also be displayed with or without treatment target sites 901.

Either while the simulations described above are running, or after the simulations have been run, data from the simulations may be displayed interactively to the user. In some embodiments, the user may view static mesh geometry overlaid with electro-anatomical maps of the patient's cardiac geometry recorded in real time by the clinician.

Figure 10:
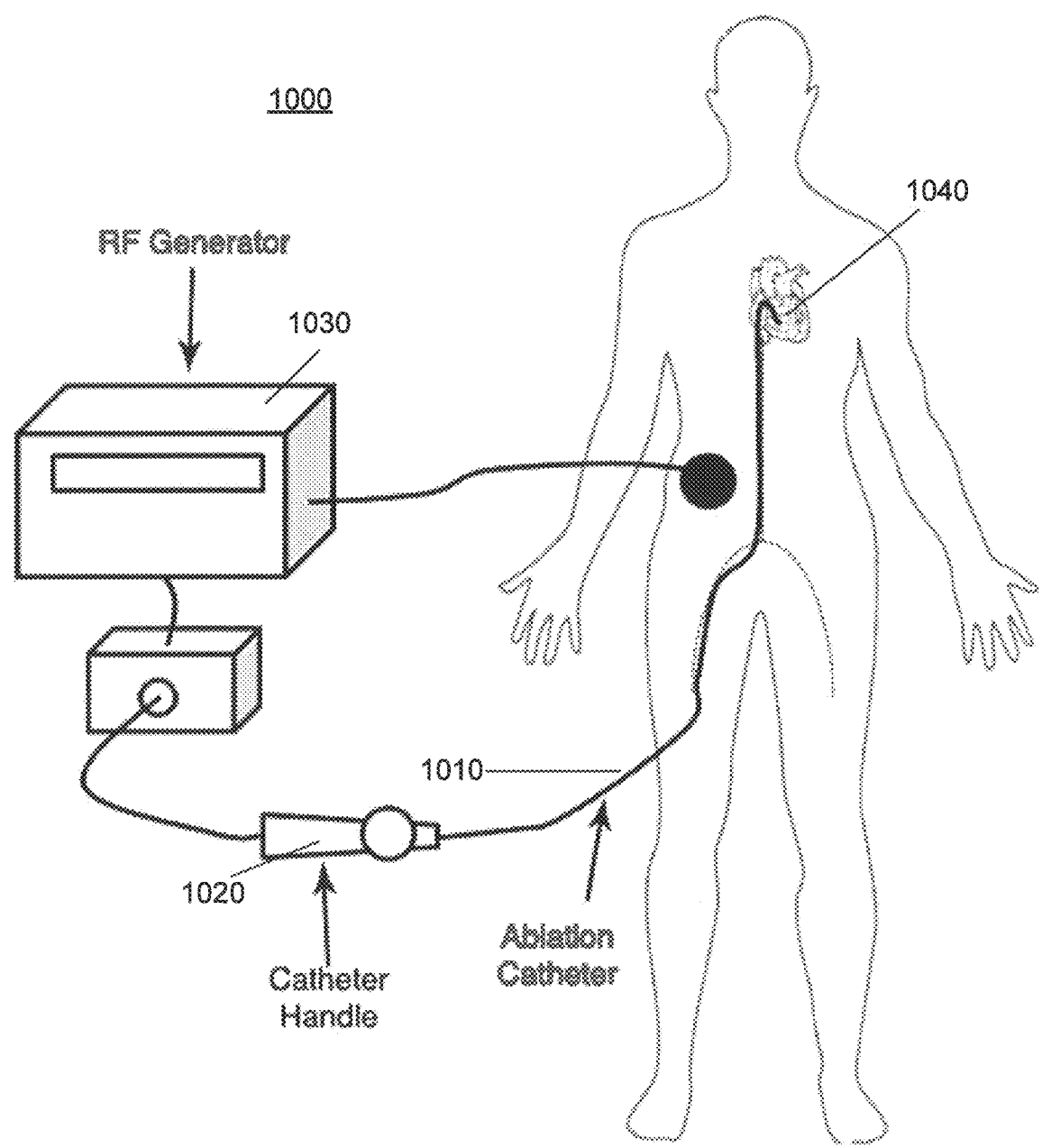
FIG. 10 illustrates components of an exemplary catheter ablation system.

Following treatment target display at step 803, a treatment target may be located during target location step 804. During target location step 804, cardiac mapping system 300 may guide a treatment catheter ablation tip 1040 to a target treatment site 901. The following description of target location step 804 and following steps pertains to the use of a catheter ablation system 1000, such as that shown in FIG. 10, to perform treatment. Additional embodiments consistent with the present disclosure may utilize other suitable treatment modalities. During target location step 804, ablation catheter 1010 may be guided into the heart. An intracardiac location of an ablation tip 1040 of ablation catheter 1010 may be displayed on a cardiac mapping and navigation system 300. Ablation tip 1040 may be displayed on the fused map of the patient's heart, showing treatment targets 901. As ablation tip 1040 nears a selected treatment target 901, the user may be provided feedback indicating a proximity of ablation tip 1040 to the treatment target.

Feedback may include one or more of several modalities. For example, feedback may be provided through catheter handle 1020, through RF generator 1030, through display 301 of mapping system 300, or through a dedicated feedback unit configured to provide a user with information about proximity of ablation tip 1040 to treatment target 901. Feedback may include audible noises, which may alter in frequency or pitch based on variance in proximity of ablation tip 1040 to treatment site 901. In some embodiments, the rate at which an audible beeping occurs may indicate greater proximity to treatment site 901, with a solid tone indicating that ablation tip 1040 has reached an optimal location. An audible noise may be emitted from catheter handle 1020, RF generator 1030, the cardiac mapping and navigation system 300, or any other device used in conjunction with catheter guidance.

Some embodiments may utilize visual confirmation on the mapping system display, for example, a change in the appearance of the catheter on the mapping system display, a glowing of the tip of the catheter, and a change in color of the displayed treatment site 901. In some embodiments, the visual display may alter gradually, for example, by altering color or adjusting a rate of flashing, dependent on the proximity of ablation tip 1040 to treatment site 901. Other visual effects indicating a correct location of the ablation tip 1040 may include blinking, change of color, change of transparency, change of hue or intensity.

In some embodiments, catheter handle 1020 may be configured to provide a tactile alarm, such as vibration dependent upon a proximity of ablation tip 1040 to treatment target site 901. In some embodiments, catheter handle 1020 may be configured to interact with another peripheral device, for example by wireless connection. A second peripheral device may include, for example, a smartphone, smart watch, or custom device that could be worn on the wrist, belt, etc.

When target location step 804 is complete, and ablation tip 1040 has reached an appropriate target treatment site 901, target treatment may be delivered during target treatment step 805. In some embodiments, target treatment delivery may include ablation of target treatment site 901. RF generator 1030 may deliver radiofrequency energy to ablation tip 1040 in order to ablate target treatment site 901. Any suitable ablation catheter 1010 and RF generator 1030 may be used for target treatment step 805. Based on the known characteristics of the ablation catheter 1010 and RF generator 1030 that are used, appropriate parameters for ablation of target treatment site 901 may be determined. For example, wattage, therapy duration, irrigation rate, target site temperature, tip pressure (contact force), etc., may be selected to produce a lesion of an appropriate size to fully ablate target treatment site 901. In some embodiments, ablation parameters may be suggested, for example by the cardiac mapping and navigation system 300 or by any suitable associated processing device, based on the selected target treatment site 901 and the catheter 1010 being used. In some embodiments, based on the selected target treatment site 901, the use of a particular type of catheter 1010 may be suggested.

Figure 11:
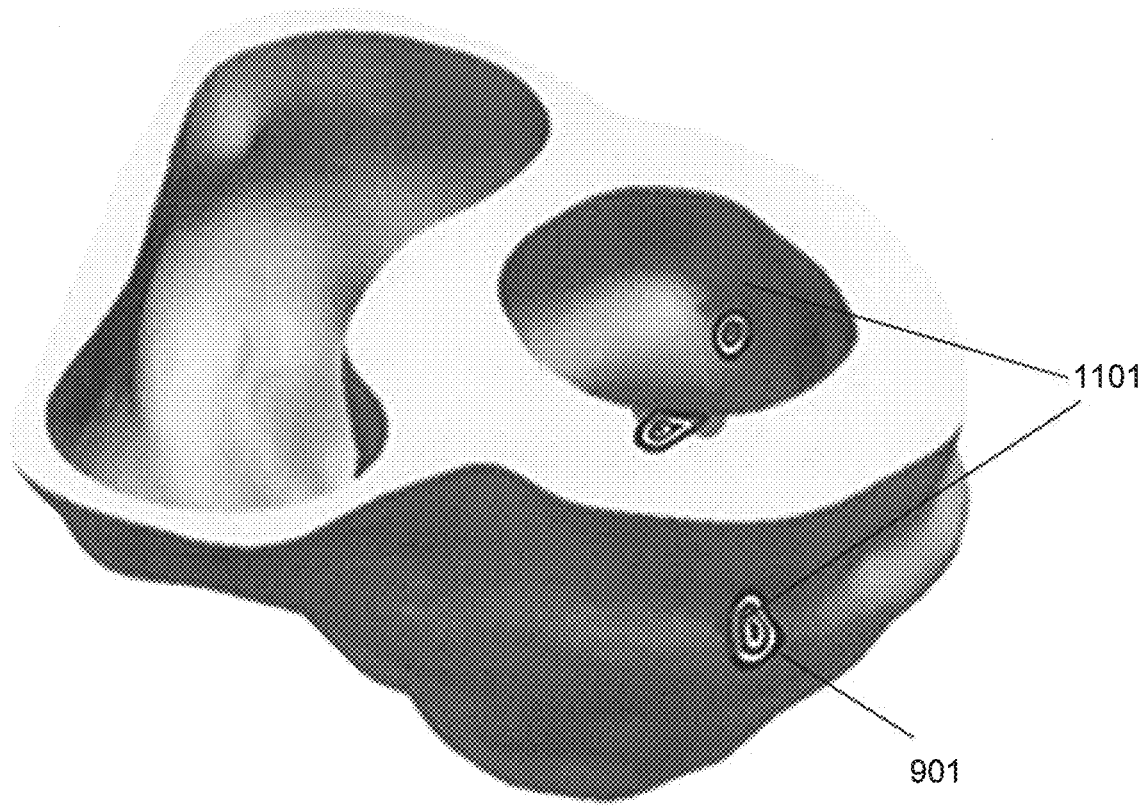
FIG. 11 illustrates an exemplary display of a treated target along with target treatment sites on a fused map.

Following target treatment step 805, treated target display step 806 may be performed to display the treatment area, for example, an ablated region, on the fused map. A size and depth of the ablated region may be estimated based on at least one of a catheter 1010 that is used, parameters of the therapy delivery, and heart properties including thermal conductivity or resistance. Ablation size and depth estimates may be based on empirical and theoretical formulas. FIG. 11 illustrates an exemplary display of treated target 1101 along with target treatment sites 901 on fused map 900. The ablated region may be shown on the display as a specific color, e.g., a red dot. The user interface may also display an overlap of target treatment sites 901 and the treated target 1101 in several additional ways. Overlap may be displayed, for example, in a color that is different than both the target treatment site 901 and the treated target 1101. It may also be shown as the same color as one of the target treatment site 901 and the treated target 1101 with at least one different visual property including, but not limited to transparency, hue, intensity, glow, or other visual properties. Treated target display step 806 may illustrate a need to conduct multiple ablations in order to fully ablate target treatment site 901. A user may repeatedly return to target location step 804 and target treatment step 805 in order to fully treat the first target treatment site 901 as well as additionally identified target treatment sites 901.

When an entire target treatment site 901 has been ablated, a user interface of the cardiac mapping and navigation system 300 may visually show the successful ablation of at least one target treatment site 901 by changing at least one visual property of the target treatment site 901 such as color, transparency, hue, intensity, glow, or other visual properties. The display of the cardiac mapping and navigation system 300 may also display text describing the successful ablation of the target treatment site 901, including but not limited to statistical metrics that may take into consideration at least one of the accuracy of the registration of target treatment site 901, the accuracy of the display of catheter 1010, accuracy of the registration of catheter 1010, and other potential sources of error in the system.

In some embodiments, display 301 of the cardiac mapping and navigation system 300 may combine visual properties with statistical metrics, for example, by employing a color gradient to display the percentage likelihood of effective treatment of a target treatment site 901. Such a display may include, for example, a red area indicating a high likelihood of successful ablation, shading through orange, yellow, and green to indicate progressively lower likelihoods of successful ablation.

The display of the cardiac mapping and navigation system 300 may also show metrics such as the percentage of all or target treatment sites 901 that have been treated, the number of treated targets 1101, the number of treated targets 1101 successfully ablated, as well as other metrics relating to the successful or unsuccessful ablation of the target treatment sites 901.

In addition to a traditional 3-D view of the heart that is shown on the cardiac mapping and navigation system 300, other views may be shown on the display of the cardiac mapping and navigation system 300, including but not limited to 2-D views in the axial, sagittal, and coronal directions. Additionally, one or more cross sectional views may be shown along any arbitrary cross section. The user interface of the cardiac mapping and navigation system 300 may allow for the user to scroll through multiple slices of the heart to see the depth of penetration of the ablation locations that have been performed. Cross-sectional views of the heart may show the desired depth of penetration of the target treatment site 901 as well as the depth of penetration of the treated target 1101 created by the catheter 1010. Comparisons between target treatment sites 901 and treated targets 1101 may be displayed in cross-sectional views in similar fashion to those outlined above with respect to the 3-D view. It may be possible that an entire surface of a target treatment site 901 is covered by the treated targets 1101, but that portions of the depth of the target treatment site 901 are not covered by the treated targets 1101. In such cases, a user interface of the cardiac mapping and navigation system 300 may suggest additional regions for treatment in order to reach the untreated portions of target treatment site 901. A cross-sectional view may be shown alone or in conjunction with other views.

In some embodiments, treated target display step 806 may further include performing additional electrical mapping on treated target site 1101 using mapping catheter 301. Mapping catheter 301 may be used to electrically map treated target site 1101 to confirm the efficacy of treatment. Information from electrical remapping may be combined with ablation size and depth estimates to provide more accurate information about the probability of success of the target treatment.

In some embodiments, resimulation step 807 may follow treated target display step 806. Resimulation step 807 may be used to update the target treatment map data. For example, once completed and assessed, information about the size, location, and depth of a treated target site 1101 may be sent to a processing device configured to generate the cardiac model and run the simulations of steps 102-108. Information about the size, location, and depth of the treated target sites may be estimated using the above-described methods, and may also be measured using in-situ MRI, catheter-based ultrasound, or other imaging modalities. The new information about additional scar tissue generated by the ablation at treated target site 1101 may be incorporated into the cardiac model generated at cardiac model generation step 104. Stimulation protocol simulation step 105 may be performed again and a new set of treatment targets 901 may be identified and processed at steps 106 and 107. The new, secondary, treatment targets may include additional, fewer, or altered treatment targets 901, based on the efficacy and accuracy of lesion placement at treated target site 1101. This process could be repeated any number of times. The resimulations may be performed locally using the computing hardware within mapping system 300, on a system adjacent to the mapping system 300, and/or on a remote system connected to the operating room by a network (LAN or WAN).

Some embodiments may further include a treatment assessment step 808. During treatment assessment step 808, a physician may attempt to induce VT in the patient's heart to determine success or failure of the treatment. Such an attempt may be made after treatment of all treatment targets 901, or after partial completion of treatment.

The present disclosure describes several treatment methods. While the disclosure may relate steps of these methods in sequential order, such description does not limit the methods disclosed herein to conducting these steps in the sequential order described. A person of skill in the art will recognize that the ordering of some steps may be altered. Additionally, some steps may be conducted simultaneously to other steps. Where certain steps require repetition, repetition may be performed before or after moving on to a subsequent step. For example, resimulation step 807 may be performed after the treatment of each treatment target site 901 during target treatment step 805, or, it may be performed only after several treatment targets 901 have been treated. Other steps described herein may similarly be adjusted without departing from the scope of this disclosure.

Additional embodiments of the disclosed system may be used for treatment of atrial fibrillation. Additionally, other treatment technologies consistent with the present disclosure, beyond radiofrequency ablation, may include cryoablation, ultrasound ablation, laser ablation, microwave ablation, argon ablation, alcohol ablation, and any other suitable ablation technology. Additionally, methods disclosed herein may be used to guide the delivery of gene therapy, for example, where gene therapy modifies the electrophysiologic properties of one or more cardiac tissues in order to prevent the initiation or maintenance of cardiac arrhythmias.

In some embodiments, by permitting a user to select stimulation protocols only, methods disclosed herein may be used to optimize locations for CRT lead placement. Under this mode of operation, the clinician may select one or more lead placements and evaluate the efficacy of any simulated improvements to one or more of cardiac output, cardiac efficiency, and hemodynamic load. Simulations may be compared with real-time ultrasound imaging to verify the efficacy of the simulated model.

In some embodiments, by permitting a user to select stimulation protocols only, methods disclosed herein may be used to assess a patient's risk of developing cardiac arrhythmias. Under this mode of operation, the clinician may select one or more programmed stimulation modes to virtually assess the likelihood that a patient will experience spontaneous cardiac arrhythmias. Simulations may be compared with other clinical variables and diagnostic tests to help guide a patient's treatment plan and inform clinical treatment choices. For example, the results of the simulation may support decision making between ICD, CRT, ablation, or medical management options for an individual patient.

The foregoing description and examples have been set forth merely to illustrate the invention and are not intended as being limiting. Each of the disclosed aspects and embodiments of the present invention may be considered individually or in combination with other aspects, embodiments, and variations of the invention. Further, while certain features of embodiments of the present invention may be shown in only certain figures, such features can be incorporated into other embodiments shown in other figures while remaining within the scope of the present invention. In addition, unless otherwise specified, none of the steps of the methods of the present invention are confined to any particular order of performance. Modifications of the disclosed embodiments incorporating the spirit and substance of the invention may occur to persons skilled in the art and such modifications are within the scope of the present invention. Furthermore, all references cited herein are incorporated by reference in their entirety.

What is claimed is:

1. A system for determining cardiac targets, the system comprising:
a non-transitory computer readable medium comprising instructions;
at least one processing device configured to carry out the instructions to:
receive cardiac imaging data;
segment the cardiac imaging data to identify at least two types of cardiac tissue;
generate a cardiac model based on the identified tissue;
simulate cardiac activity based on the generated cardiac model;
locate at least one cardiac target based on the simulation; and
assign, to the at least one cardiac target based on the simulation, at least one of a risk factor or a success factor of a simulated ablation of the at least one cardiac target.

2. The system of claim 1, wherein the at least one processing device is further configured to carry out the instructions to:
display the cardiac target location on a cardiac mapping system.

3. The system of claim 1, wherein the at least one processing device is further configured to carry out the instructions to:
guide a treatment catheter to the cardiac target location.

4. The system of claim 1, wherein the cardiac imaging data is obtained from at least one of magnetic resonance imaging, computed tomography, echocardiogram, and positron emission tomography.

5. The system of claim 1, wherein segmenting the cardiac imaging data includes identifying at least two of scar tissue, border tissue, and healthy tissue.

6. The system of claim 1, wherein generating the cardiac model includes generating a finite mesh.

7. The system of claim 1, wherein simulating cardiac activity includes:
selecting at least one model stimulation site;
selecting stimulation parameters for each selected model stimulation site; and
simulating cardiac activity based on the stimulus for the at least one model stimulation site,
wherein the at least one model stimulation site and the stimulation parameters are selected to simulate a cardiac disorder.

8. The system of claim 7, wherein the cardiac disorder includes at least one of ventricular tachycardia and atrial fibrillation.

9. The system of claim 1, wherein the at least one cardiac target is a cardiac location that, when treated in the cardiac model, alters one or more parameters associated with the simulated cardiac activity.

10. The system of claim 1, wherein the at least one cardiac target is a target for ablation therapy.

11. The system of claim 1, the at least one processing device is further configured to carry out the instructions to:
update the cardiac model based on the simulated ablation of the at least one identified cardiac target; and
resimulate cardiac activity based on the updated model.

12. The system of claim 1, wherein the at least one cardiac-target includes a plurality of cardiac treatment location groups, each location group including at least one cardiac treatment target and being selected to alter the simulation of cardiac activity.

13. The system of claim 1, wherein the processing device is further configured to carry out the instructions to identify at least one alternate cardiac treatment location if the at least one of the risk factor or the success factor exceeds a predetermined threshold.

* * * * *